(12) United States Patent  
Walls et al.

(10) Patent No.: US 9,201,026 B2  
(45) Date of Patent: Dec. 1, 2015

(54) METHOD AND SYSTEM FOR ESTIMATING PROPERTIES OF POROUS MEDIA SUCH AS FINE PORE OR TIGHT ROCKS

(71) Applicant: Ingrain, Inc., Houston, TX (US)

(72) Inventors: Joel Walls, Houston, TX (US); Elizabeth Diaz, Houston, TX (US); Michael Suhrer, Houston, TX (US); Boaz Nur, Houston, TX (US); Avrami Grader, Houston, TX (US); Gustavo Carpio, Houston, TX (US); Timothy Cavanaugh, Houston, TX (US); Marcus Ganz, Houston, TX (US)

(73) Assignee: Ingrain, Inc., Houston, TX (US)

( * ) Notice: Subject to any disclaimer, the term of this patent is extended or adjusted under 35 U.S.C. 154(b) by 345 days.

(21) Appl. No.: 13/850,543

(22) Filed: Mar. 26, 2013

(65) Prior Publication Data

US 2013/0259190 A1  Oct. 3, 2013

Related U.S. Application Data

(60) Provisional application No. 61/617,099, filed on Mar. 29, 2012.

(51) Int. Cl.
*G01N 23/04* (2006.01)
*G01N 23/22* (2006.01)
(Continued)

(52) U.S. Cl.
CPC .............. *G01N 23/046* (2013.01); *G01N 23/22* (2013.01); *G01N 33/24* (2013.01); *G01N 33/2823* (2013.01); *G01N 15/088* (2013.01)

(58) Field of Classification Search
CPC ................... G06T 7/0004; G06T 2207/10081; G06T 2207/30108; G06T 2207/20152; G06T 7/0081; G06T 17/05; G06T 2207/10056; G06T 2207/20016; G06T 2207/20148; G06T 7/602; G06T 17/30; G06T 2207/10061; G01N 15/088; G01N 23/046; G01N 23/22; G01N 33/24; G01N 33/2823; A61B 6/482; A61B 6/032; A61B 6/405; A61B 6/4014; A61B 6/4035; A61B 6/025; A61B 6/4233; A61B 6/481; A61B 6/505; A61B 6/4241; A61B 6/4441; A61B 6/466; A61B 6/488; A61B 6/504; A61B 6/5235; A61B 6/4085; A61B 6/12; A61B 6/04
USPC ................. 378/9, 46, 50, 53, 54, 70; 382/109
See application file for complete search history.

(56) References Cited

U.S. PATENT DOCUMENTS 6,516,080 B1   2/2003  Nur
2009/0288880 A1  11/2009  Wojcik et al.
(Continued)

OTHER PUBLICATIONS

Huang, J., "Simultaneous Multi-channel Data Acquisition in Three Dimensions," printout accessed at: http://www.zeiss.de/C1256E4600307C70/EmbedTitelIntern/AN_Simultaneous_Multichannel_Data_Acquisition_in_Three_Dimensions_neu/$File/AN_Simultaneous_Multichannel_Data_Acquisition_in_Three_Dimensions.pdf, Carl Zeiss, Mar. 2011, pp. 1-4.
(Continued)

*Primary Examiner* — Irakli Kiknadze
(74) *Attorney, Agent, or Firm* — Kilyk & Bowersox, P.L.L.C.

(57) ABSTRACT

A method for estimating properties of porous media, such as fine pore or tight rocks, is provided. The method comprises digital image scanning of sequential sub-samples of porous media at progressively higher resolution to systematically identify sub-sections of interest within the original sample and then estimate properties of the porous media. The resulting properties of the porous media then can be optionally upscaled to further estimate the properties of larger volumes of the porous media such as rock facies or subterranean reservoirs. A system operable for conducting the method also is provided.

50 Claims, 12 Drawing Sheets

(51) Int. Cl.
*G01N 33/24* (2006.01)
*G01N 33/28* (2006.01)
*G01N 15/08* (2006.01)

(56) References Cited

U.S. PATENT DOCUMENTS

| | | | |
|---|---|---|---|
| 2010/0215249 A1* | 8/2010 | Heitz | G06T 7/0075 382/154 |
| 2013/0028371 A1 | 1/2013 | Derzhi | |
| 2013/0073207 A1 | 3/2013 | Ganz | |
| 2013/0094716 A1* | 4/2013 | Carpio et al. | 382/109 |
| 2013/0236064 A1* | 9/2013 | Li et al. | 382/109 |

OTHER PUBLICATIONS

Sisk, C., et al., "3D Visualization and Classification of Pore Structure and Pore Filling in Gas Shales," Society of Petroleum Engineers Annual Techn. Conf. & Exhibit, Florence Italy, SPE 134582, Sep. 2010, pp. 1-4.

Curtis, M. E., et al., "Structural Characterization of Gas Shales on the Micro- and Nano-Scales," Canadian Unconventional Resources & Int'l Petroleum Conf., Calgary, Alberta, Canada, CUSG/SPE 137693, Oct. 2010, pp. 1-15.

Milner, M., et al., "Imaging Texture and Porosity in Mudstones and Shales: Comparison of Secondary and Ion-Milled Backscatter SEM Methods," Canadian Unconventional Resources & Int'l Petroleum Conf., Calgary, Alberta, Canada, CUSG/SPE 138975, Oct. 2010, pp. 1-10.

Wellington, S. L., et al., "X-Ray Computerized Tomography," Journal of Petroleum Technology, Aug. 1987, pp. 885-898.

Gardner, J. S., et al., "Litho-Density Log Interpretation," SPWLA Twenty-First Annual Logging Symposium, Jul. 1980, pp. 1-23.

Knackstedt, M. A., et al., "Properties of Reservoir Core Derived from 3D Images," Society of Petroleum Engineers Asia Pacific Conference on Integrated Modeling for Asset Management, Kuala Lumpur, Malaysia, SPE 87009, Mar. 2004, pp. 1-14.

Zhang S., et al., "The Analysis and Simulation of Rock Properties Using FIB-SEM and Virtual Material Studio," Proceedings of the 2011 NAFEMS World Congress, Mar. 2011, pp. 1-12, XP055067172.

Passey, Q. R., et al., "From Oil-Prone Source Rock to Gas-Producing Shale Reservoir—Geologic and Petrophysical Characterization of Unconventional Shale-Gas Reservoirs," Proceedings of the 2010 CPS/SPE International Oil & Gas Conference and Exhibition, Beijing, China, SPE 131350, Jun. 2010, pp. 1-29, XP055067055.

Suher, M., et al., "Imaging and Computing the Physical Properties of Gas Shale," Proceedings of the 2010 GeoCanada Conference—Working With the Earth, May 2010, pp. 1-4, XP055067132.

"PCT Invitation to Pay Additional Fees and Where Applicable, Protest Fee" including citations of documents considered to be relevant for PCT/US2013/033810, dated Jun. 25, 2013, 4 pages.

International Search Report and Written Opinion issued in corresponding International Patent Application No. PCT/US2013/033810 dated Aug. 29, 2013 (20 pages).

Walls et al., "Digital Rock Physics Provide Critical Insights to Characterize Eagle Ford," The American Oil & Gas Reporter, Feb. 2011 (4 pages).

Walls et al., "Relationship of shale porosity-permeability trends to pore type and organic content," Denver Well Logging Society, Proceedings of the 2011 Fall Workshop "Petrophysics in Tight Oil," Denver, CO, Oct. 26, 2011 (12 pages).

Remeysen et al., "Application of microfocus computed tomography in carbonate reservoir characterization: Possibilities and limitations," Marine and Petroleum Geology, vol. 25, 2008, pp. 486-499.

* cited by examiner

| clay | pore | organic | calcite | qtz | plagioclase | pyrite | TiO2 | Total |
|---|---|---|---|---|---|---|---|---|
| 27.7 | 1.7 | 7.2 | 48.7 | 4.3 | 8.1 | 2.2 | 0.1 | 100 |
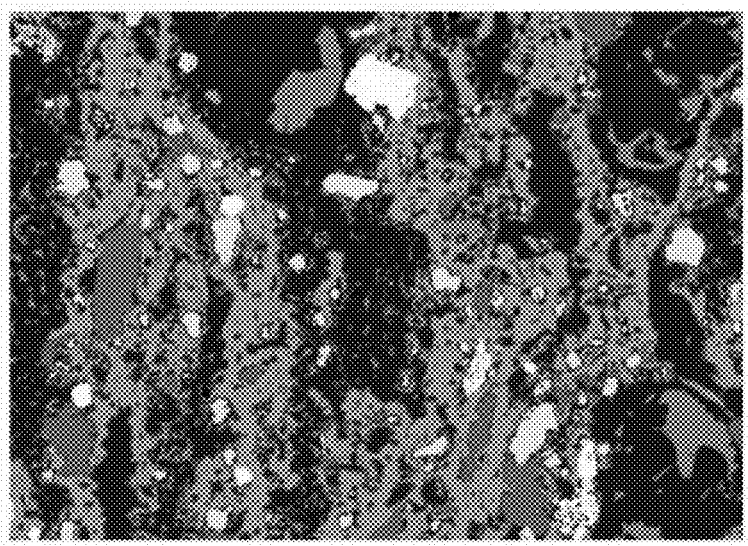
Figure 7c
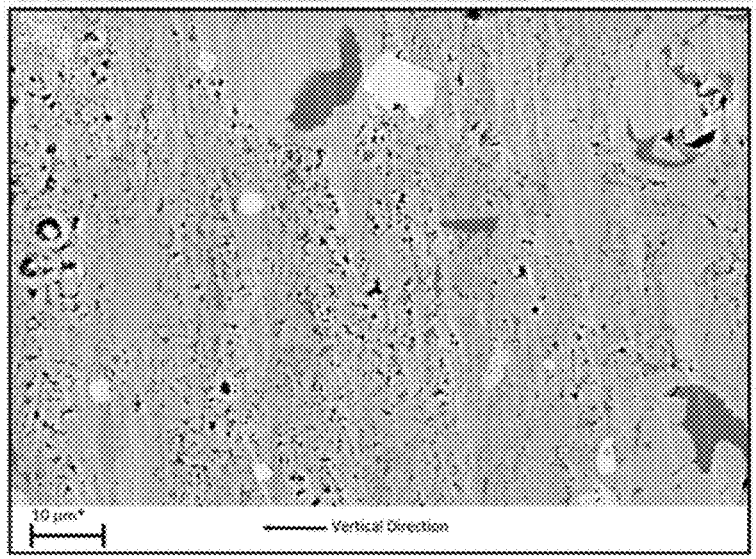
Figure 7b
Figure 7a

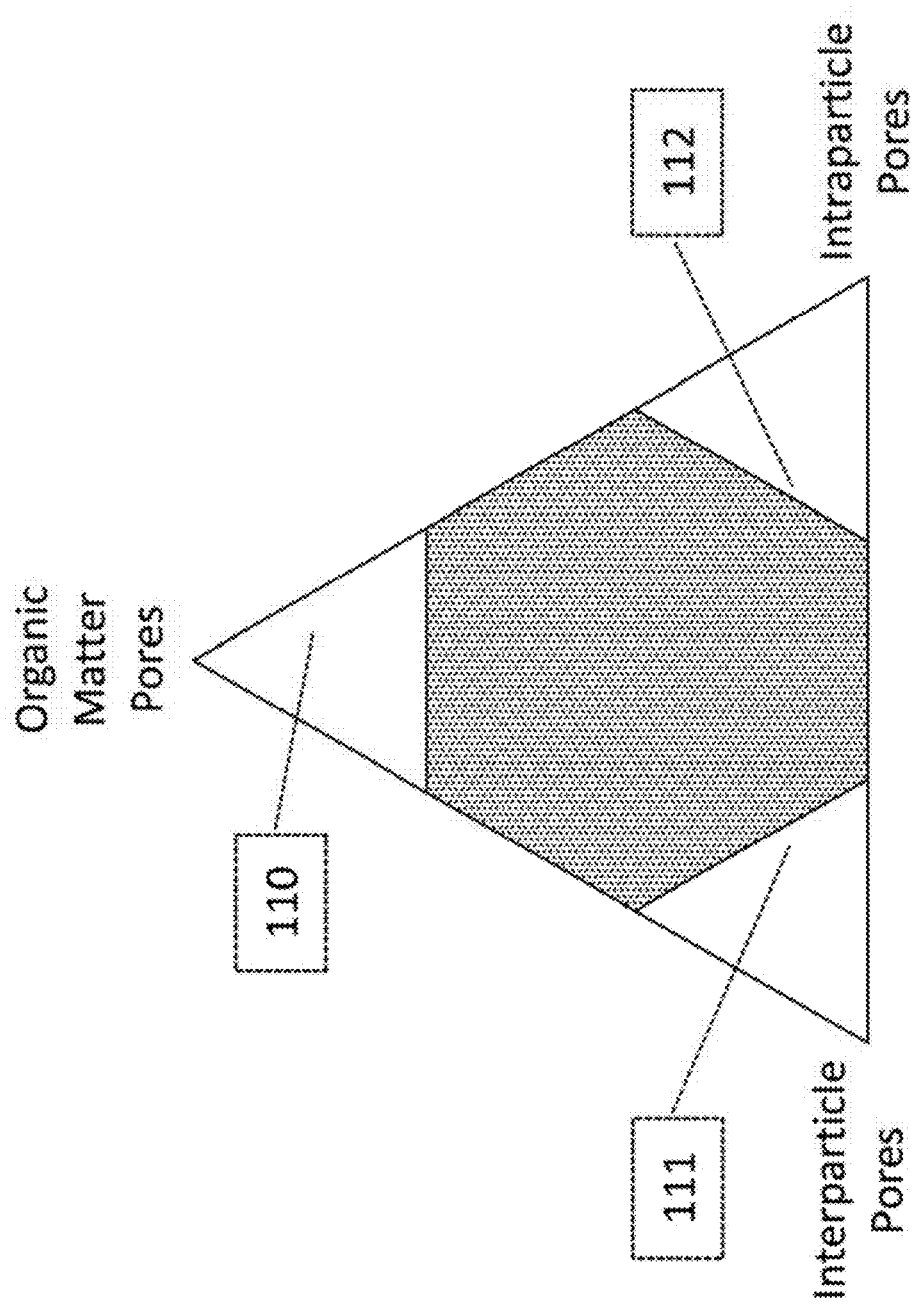

METHOD AND SYSTEM FOR ESTIMATING PROPERTIES OF POROUS MEDIA SUCH AS FINE PORE OR TIGHT ROCKS

This application claims the benefit under 35 U.S.C. §119 (e) of prior U.S. Provisional Patent Application No. 61/617,099, filed Mar. 29, 2012, which is incorporated in its entirety by reference herein.

BACKGROUND OF THE INVENTION

This invention relates to the field of digital rock physics and, more particularly, to methods to estimate geophysical properties of rocks which can include those with very fine pore structures such as shales.

The present invention relates to a method and system to analyze a porous medium with very fine pores, such as a shale reservoir rock sample, to obtain values of porosity, permeability, total organic content, and other geophysical data. Shale is an unconventional source of oil and/or gas. Shale rocks have not been studied extensively due to the fact that they traditionally were thought of as the source rock and not a potential reservoir because of their low porosity and permeability values. However, there are new methods to extract the oil and gas within these rocks, and therefore, there is great interest in analysis methods to characterize these rocks to better understand the mechanics of production from shales.

Traditionally, there were only limited ways to analyze shale samples, and this began with scanning electron microscopes (SEM). The SEM image provides a two-dimensional (2D) picture or image of the sample that typically has a resolution of approximately 15-100 nanometers. Using only two-dimensional images, however, one is only able to estimate porosity and organic content, and one can only approximate permeability because permeability is a three dimensional property.

In scanning electron microscopy (SEM), multitudes of electrons are generated as the result of the energetic bombardment of a primary electron beam (PE) directed on the sample, such as illustrated in FIG. 1. These generated electrons can carry distinct structural information of the sample, and can differ from one another in origin, energy and traveling direction. For example, type-I secondary electrons (SE-1) emit with a high angle at a close proximity from the impact point of the primary electron beam (PE), and carry high-resolution, surface sensitive information of the sample. Type-II secondary electrons (SE-2) are generated from a deeper and wider volume of the sample surface than the type-I secondary electrons (SE-1s), and emit from the sample surface with a lower angle trajectory, and carry intrinsically lower resolution, topographical information. Similarly, singly scattered backscattered electrons (BSE-1) tend to emit at a high angle and are closely linked to compositional contrast, while multiply-scattered BSEs (BSE-2) emit from the sample surface at a lower angle trajectory, and their yields represent a mixture of composition and crystalline structures of the sample. Different detectors associated with the SEM system can be used to collect these different electrons. The detected electrons can be processed to generate an image of the scanned region of the sample. These and other details about SEM imaging are described, for example, in Huang, J., "Simultaneous Multichannel Data Acquisition in Three Dimensions", http://www.zeiss.de/C1256E4600307C70/EmbedTitelIntern/AN_Simultaneous_Multichannel_Data_Acquisition_in_Three_Dimensions_neu/$File/AN_Simultaneous_Multichannel_Data_Acquisition_in_Three_Dimensions.pdf, Carl Zeiss, 2011.

Along with technological advances and use of medical equipment to help analyze geologic features, advances in workflow have been created. For example, a workflow has been shown which has three basic steps of (a) 3D CT imaging and/or FIB-SEM (focused ion beam combined with SEM) imaging; (b) segmentation of the digital volume to quantitatively identify the components, including the mineral phases, organic-filled pores, and free-gas inclusions; and (c) computations of TOC (Total Organic Content), porosity, pore connectivity, and permeability in the three axis. Sisk et al, SPE 134582, "3D Visualization and Classification of Pore Structure and Pore Filling in Gas Shales", 2010. Using FIB-SEM technology, a sample is analyzed in three dimensions by creating a plurality of two-dimensional images. The segmentation process can be done by, assigning gray scale ranges to features, and volumes can be constructed which show three dimensional distributions of these features. Curtis et al, SPE 137693, "Structural Characterization of Gas Shales on the Micro- and nano-Scales", 2010. The features that are present within the rock can include, but are not limited to, pores, organic matter, and rock matrix. The process of analyzing shale rocks in three dimensions has greatly aided understanding of how a complex shale reservoir functions.

To enhance image quality, new preparation techniques have been proposed, such as those shown by Milner et al, SPE 138975, "Imaging Texture and Porosity in Mudstones and Shales: Comparison of Secondary and Ion-Milled Backscatter SEM methods", 2010. Milner et al. shows two preparation techniques which were used for SEM imaging, wherein secondary electron images represent fresh, minimally gold-coated surfaces broken normal to bedding, and backscatter images show milled surfaces approximately 1.0 mm by 0.5 mm, created using a JEOL IB-9010 Argon-ion polisher. Both secondary and milled backscatter samples were imaged using a FEI NovaNano 630 field emission scanning electron microscope. An Argon ion polisher is used to polish the sample, so the image appears cleaner, and therefore is easier to segment. Following the polishing step, the sample is coated with gold, and then processed and imaged with an FIB-SEM. Within the SEM column there are two detectors, the ESB (BSE-1) and the SE-2. The two detectors help eliminate the shortfalls of only using one detector. When using only one detector, only one image is created, and it is difficult to discriminate between porosity, organic materials such as kerogen, and minerals. By using two detectors the SEM produces two different views of the sample, making it possible to quantify solid materials and pore space.

Previously, the assignee's inventors developed an improved image segmentation process, which is described in U.S. Patent Application No. 61/547,090, which is incorporated herein in its entirety by reference. This technique involves simultaneously creating two SEM images of the surface of a porous medium. One image is produced by detecting primary backscattered electrons (ESB) and a second image is produced by detecting secondary electrons (SE-2). These two images have different qualities in that the SE-2 produced images provide clear distinction of pore walls but organic content contained within the pores such as kerogen, distort the image resulting in estimates of porosity that are too low. The BSE produced image provides a different perspective on contained organic content and by aligning and analyzing these two images, a more accurate picture of pore space and organic content results.

In addition to these procedures, X-ray Diffraction (XRD) is commonly used to determine chemical composition and crystallographic structure of shales. XRD yields the atomic structure of materials and is based on the elastic scattering of X-rays from the electron clouds of the individual atoms in the system. As also described by the indicated Milner et al. document (SPE 138975), XRD data were generated from powdered samples analyzed with a Figaku Ultima III X-ray diffractometer, and results were interpreted using JADE software.

Large samples of porous rock are required in order to obtain estimates of rock properties such as permeability, porosity, elasticity and other properties that are typical of an entire subterranean rock formation or facies. One common sample used to estimate rock properties is a well core. Well cores are very small compared to an entire formation, so multiple well cores are typically taken, analyzed, and rock properties are interpolated in between geographic locations of the cores. When rock properties are estimated using digital rock physics, the problem of sample size versus formation or facies size is even greater. Digital rock physics techniques for estimating rock properties have the advantage that they can accurately produce digital images of very fine pore structures and identify small volumes of organic materials present in the pore structure of the rock. However, it is very time consuming and expensive to digitally scan very large samples to estimate rock properties. The difference in scale between the sample (core) and the pores contained in the sample can complicate pore analysis thereof. Scanning the entire sample at a resolution high enough to identify all of the pores can result in a complete assessment of the pore structure of the sample. However, scanning the entire sample at a resolution high enough to identify all of the pores is not practical due to the time and expense required to do a complete scan.

The present investigators have recognized that FIB-SEM systems work on relatively small sample size and as such, an efficient method is needed to initially overview or scout for areas of interest in analyzing a shale reservoir and then move to higher and higher magnifications (resolutions) on identified areas of interest. The present investigators further recognized that manual selection of rock samples for high resolution analysis can provide the geologist or reservoir engineer information about facies that are likely to contain organic matter, but the manual methods can be highly subjective, inconsistent, and expensive. The present investigators further have recognized that there is a need for a method of high resolution analysis of rock samples which incorporates reliable automated sample screening and analysis features.

SUMMARY OF THE INVENTION

A feature of the present invention is a method and a system to estimate values of porosity, permeability, organic content and/or other relevant rock properties through analysis of rock samples, such as organic mud rocks commonly referred to as shale.

A further feature of the present invention is a method and a system to help select the best subsample from a larger sample that will characterize the whole rock or will be representative of rock facies containing hydrocarbons.

A further feature of the present invention is a method and a system to prepare rock samples for analysis using digital rock physics.

A further feature of the present invention is a method and system to estimate rock properties in a time frame which is short enough in duration for use during well drilling or completion.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates in part to a method for estimating selected physical properties of a rock sample which comprises steps of (a) preparing a rock sample, (b) creating a digital image of the rock sample by scanning the rock sample, (c) estimating the selected physical properties of the rock sample from the digital image of the rock sample, (d) determining if the digital image provides sufficient detail for estimation of final rock properties, wherein step (e) directly follows step (d) if sufficient detail is not determined to be provided and step (j) directly follows if sufficient detail is determined to be provided in step (d), (e) identifying one or more regions within the rock sample that contain high porosity and/or organic matter content, (f) selecting sub samples of the rock sample that contain high porosity and/or organic content, (g) preparing rock sub-samples from the selected subsamples, (h) increasing the resolution of the scanning of the rock sample, (i) repeating steps (b) through (d) until a desired resolution is achieved, and (j) estimating final rock properties.

The present invention further relates in part to a method for estimating selected physical properties of a rock sample, comprising (a) acquiring a physical sample of a porous medium (Sample 1), (b) performing a dual energy X-ray CT scan of Sample 1, (c) creating 3D digital images (Image 1) of Sample 1 from the dual energy X-ray CT scan, (d) calculating the bulk density, RhoB, and effective atomic number, $Z_{eff}$, for each layer of voxels (Slices) in Image 1, (e) selecting a region of interest of the Slices of Image 1 comprising selected values of RhoB and $Z_{eff}$, (f) creating physical sub-samples (Sample 2) from selected Slices of Sample 1 wherein the Slices comprise selected values of RhoB and $Z_{eff}$, (g) scanning Sample 2 with a micro CT X-ray scanner or imaging Sample 2 using a micro X-ray projection, (h) creating 2D or 3D digital images (Image 2) of Sample 2, (i) calculating porosity or RhoB and $Z_{eff}$ of Image 2, (j) selecting regions of interest of pixels or voxels from Image 2 wherein such regions of interest have relatively high porosity or selected values of RhoB and $Z_{eff}$ (Image 2), (k) creating sub-samples (Sample 3) from the physical locations corresponding to Image 2, (l) preparing Sample 3 for SEM imaging, (m) creating 2D digital images (Image 3) of Sample 3 using an SEM or SEM with EDS capability, (n) estimating porosity of Image 3, and (o) estimating organic matter content from Image 3. The method can further comprise (p) selecting regions of interest of pixels from Image 3 wherein such regions of interest have combinations of properties of interest, for example those regions comprising relatively high porosity and high organic matter content, (q) imaging physical locations of regions of interest of pixels from Image 3 wherein such regions of interest have combinations of properties of interest comprising relatively high porosity and high organic matter content with a FIB SEM using two or more detectors, (r) creating 3D digital images from the two or more detector images, (s) segmenting the two or more digital detector images to identify voxels as pore, rock or organic matter and (t) estimating rock properties from the segmented two or more detector images.

The present invention further relates in part to a method for qualitative facies analysis and selecting a subsample for estimating selected physical properties of a rock sample, comprising a) estimating values of the bulk density, RhoB, and effective atomic number, $Z_{eff}$, for layers of voxels (Slices) in 3D digital tomographic images (Image 1) of a physical sample (Sample 1), b) plotting pairs of the values of RhoB and $Z_{eff}$ on a cross plot, c) dividing the crossplot into a plurality of quadrants, and d) selecting pairs of values of RhoB and $Z_{eff}$ from one of the plurality of quadrants which correspond to a selected region of interest of the Slices of Image 1.

The present invention further relates in part to a system for estimating selected physical properties of a rock sample, comprising (a) a sample of a porous medium such as rock, (b) a dual energy X-ray CT scanner, (c) a micro X-ray CT scanner or a dual energy micro X-ray CT scanner, (d) cutting, milling or shaping devices to extract samples of porous media, (e) grinders, millers, polishers or similar devices to prepare the surface of the porous media, (f) an ion beam polisher, (g) a scanning electron microscope, and (h) one or more computer systems.

It is to be understood that both the foregoing general description and the following detailed description are exemplary and explanatory only and are only intended to provide a further explanation of the present invention, as claimed.

The accompanying drawings, which are incorporated in and constitute a part of this application, illustrate some of the features of the present invention and together with the description, serve to explain the principles of the present invention. The drawings are not necessarily drawn to scale. Like numerals in the drawings refer to like elements in the various views.

BRIEF DESCRIPTION OF DRAWINGS

FIG. 7a is an SEM image and FIG. 7b is an energy dispersive X-ray spectra for a shale rock sample, and FIG. 7c is a legend and table of materials in FIG. 7b, according to an example of the present invention.

FIG. 8 is a ternary diagram illustrating the distribution of interparticle pores, intraparticle pores, and organic matter pores in a porous rock sample, according to an example of the present invention.

DETAILED DESCRIPTION OF THE PRESENT INVENTION

The present invention relates in part to a method for estimating properties of porous media, such as fine pore or tight rocks. A method is provided to estimate values of porosity, permeability, organic content, and other relevant rock properties through analysis of rock samples, such as organic mud rocks, which are commonly referred to as shale. Digital image scanning of sequential sub-samples of porous media at progressively higher resolutions can be used to systematically identify sub-sections of interest within an original rock sample which have sufficient image detail for estimation of rock properties of the porous media. A method of the present invention can assist in the selection of the best subsample from a larger sample that can characterize the whole rock or can be representative of rock facies containing hydrocarbons. The properties estimated for the porous media then can be optionally upscaled to further estimate the properties of larger volumes of the porous media, such as rock facies or subterranean reservoirs. The types of rock to which a method of the present invention can be applied are not necessarily limited. The rock sample can be, for example, organic mud rock, shale, carbonate, sandstone, limestone, dolostone, or other porous rocks, or any combinations thereof.

Figure 1:
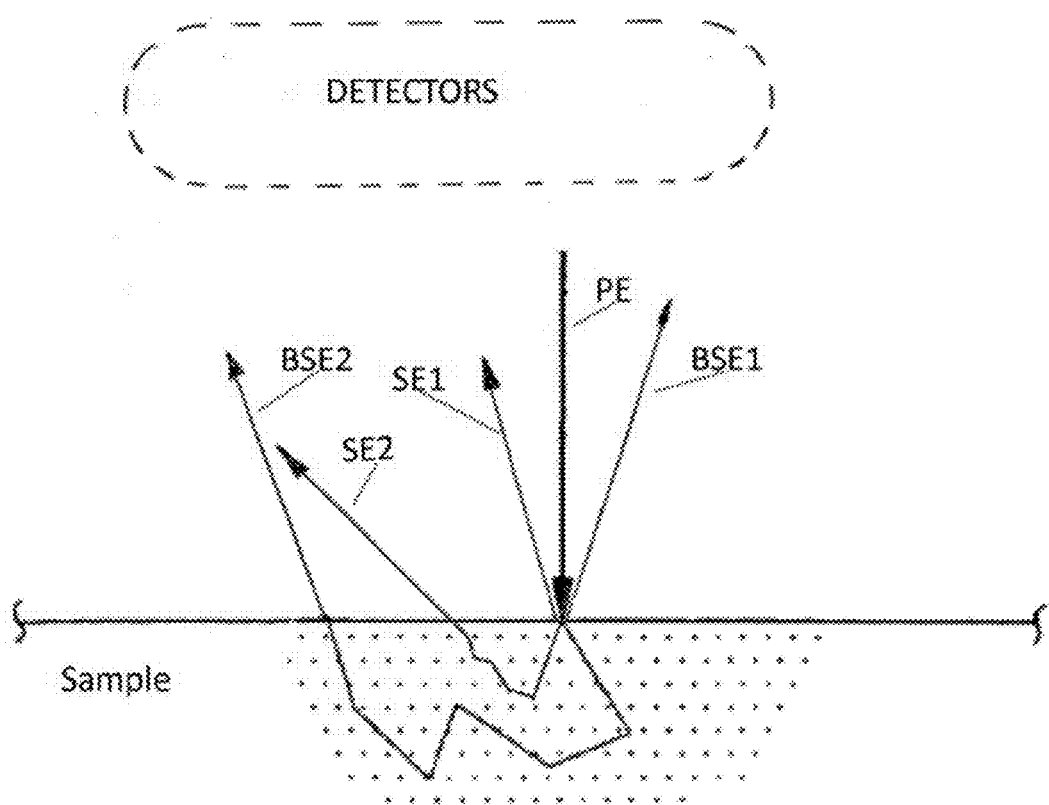
FIG. 1 is an illustration of a beam-sample interaction in scanning electron microscopy, wherein different types of electrons are emitted when a sample is excited by the primary electron beam.
Figure 2:
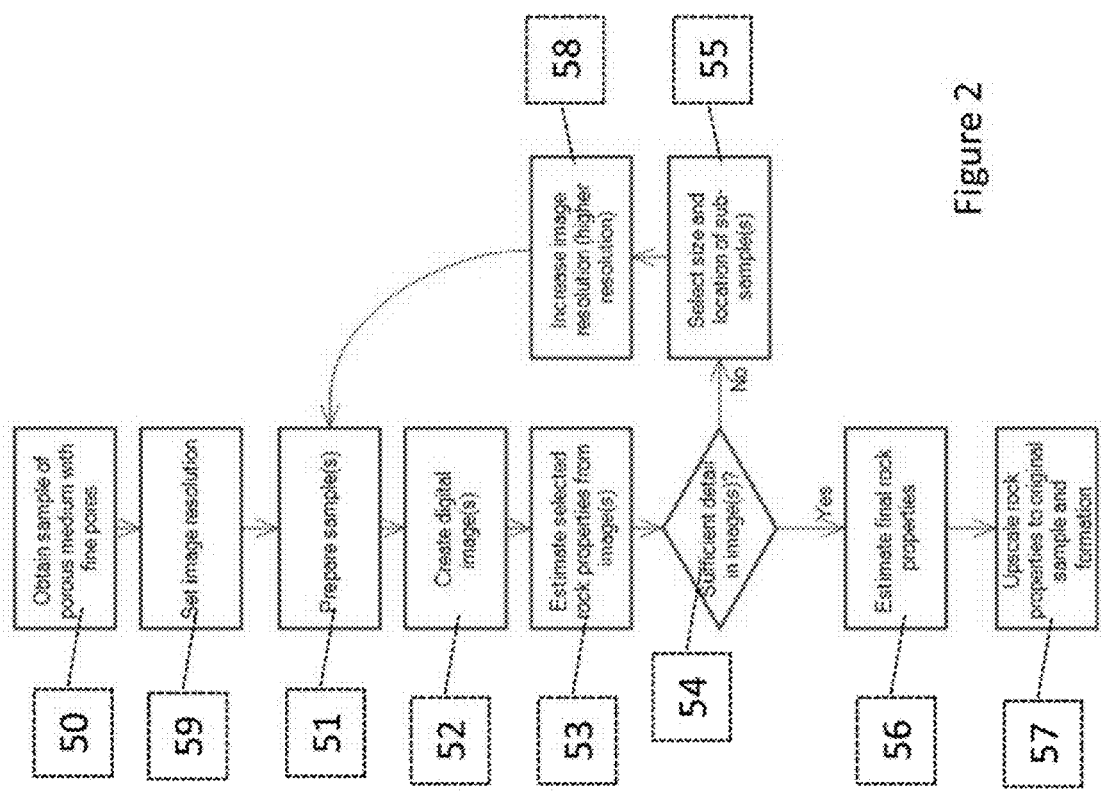
FIG. 2 is a flow chart describing a method according to an example of the present invention.

In FIG. 2, a method of the present invention is shown which includes steps (50)-(59), and arrows which show a progression of the steps. In step (50), a sample of a porous medium is obtained. Samples can include well cores, drill cuttings, or other samples obtained from subterranean rock formations or other rock formations. In step (59), an initial image capture resolution is selected on an image capture device to be used for capturing digital images of the sample, and an appropriate instrument is selected to analyze the pore structure of the sample. These initial image capture resolution selections (settings) can be based on a physical examination of the sample. Initial resolutions used in the method can be preselected based on the type, location source, or other readily identifiable aspects of the sample. For example, preselected starting resolutions for use on a given image capture device can be assigned to certain types of rock samples, source locations, or other aspects or combinations thereof. For example, for a shale rock sample, and an X-ray CT scan instrument such as described herein, the initial capture image resolution can be from about 0.2 mm to about 0.5 mm. For a shale rock sample and a focused ion beam-scanning electron microscopy (FIB-SEM) instrument such as described herein, the initial capture image resolution can typically be from about 5 nm to about 30 nm, but this range can vary between 2.5 nm to 100 nm. Time typically is the limiting factor. In step (51), selected samples can be prepared for testing to create a digital image thereof. The image can be a two-dimensional (2D) or three-dimensional (3D) image. For the FIB/SEM instrument, the 2D images are processed in a stack to create a 3D volume. In step (51), the rock sample is prepared for digital image scanning. The type of sample preparation can depend upon the image capture method to be used. For example, samples can be cleaned, shaped, mounted, or prepared with other techniques typically used for preparing a rock sample for image capture on the type of image scanning instrument to be used. In step (52), a digital image of the sample is created. Digital images can be created, for example, by X-ray computed tomography (CT) scan, dual energy X-ray computed tomography, X-ray projection, scanning electron microscopy (SEM), focused ion beam scanning electron microscopy (FIB-SEM), or other techniques that digitize rock structure to create 2D digital images or 3D digital images, or any combinations thereof. A 3D SEM volume from the sample can be constructed from a stack of closely spaced 2D images. Segmentation can be conducted on a 2D image-by-image basis. 2D Images can be segmented to classify pixels or voxels within the image. For example, segmentation can include classification as grain, pore, organic matter, mineral type or other classification. In step (53), selected rock properties can be estimated using the digital image(s) as input. The estimated selected rock properties can include, for example, bulk density (RhoB), effective atomic number ($Z_{eff}$), porosity, mineralogy, and/or permeability, or other rock properties. The selected rock properties can be used as indicators of locations within the rock where both organic matter and porosity exist. The degree of resolution required in the test can depend upon the range of pore sizes present in the rock sample. For example, a distribution of pore sizes in a rock sample that includes pores sizes that are smaller than the selected resolution may not provide sufficient detail to permit the 2D images thereof to be reliably and accurately analyzed for content. The detailed pore sizes acquired in image resolutions between about 5 nm to 30 nm in shale rocks provide sufficient detail to estimate rock properties as noted above. Pore sizes below this image resolution are not included in the estimated rock property solutions derived utilizing this method. In step (54), if sufficient detail is determined to be present in the image at the current resolution of the test, then final rock properties can be calculated. A single criterion or multiple criteria can be applied in step (54). For step (54), a criterion for determining if there is sufficient detail in the image such that the image is suitable to calculate final rock properties can be estimated. As shown in Step (55), if it is determined in step (54) that there is not sufficient detail in the image or if the image is not otherwise suitable to calculate final rock properties, then one or more locations and sizes can be selected for sub-samples from the sample previously tested for re-imaging at higher resolutions before re-estimating the selected rock properties and checking again for sufficient detail in the images captured at higher resolution than the previous iteration. For example, if insufficient detail is determined in step (54) for the image or images of the sample to proceed to estimation of final rock properties in step (56), image resolution is increased (e.g., 10% or more) in step (58) for imaging of subsamples which are selected, and then steps (51) through (54) can be repeated. In step (55), the selected size of a rock sample is suitable for the type of test to be performed on the sub-sample. The preparation of the sub-samples can comprise cutting, abrading, shaping, milling, focused ion beam polishing, other techniques to alter the size and shape of rocks, or any combinations thereof. For samples determined to have insufficient detail in the image in step (54), steps (51) through (54) can be repeated on subsamples thereof with progressively increased resolution selected in step (58) using the same or substantially the same increments of increased resolution for each iteration through the loop, or a different progression of incremental increases, until sufficient detail in the image is achieved in step (54). For example, for a shale rock sample and an X-ray CT scan instrument such as described herein, the initial capture image resolution can be as indicated and an incremental increase in resolution applied in step (58) can be from about 0.5 mm to about 2.0 mm. For a shale rock sample and a focused ion beam scanning electron microscopy (FIB-SEM) instrument, such as described herein, the initial capture image resolution can be as indicated, and the incremental increase in resolution applied in step (58) can be from about 5 nm to about 30 nm. Steps (51) through (54) can be used at least once, or repeated as many times as necessary via loop steps (55) and (58) to select suitable samples or sub-samples and achieve resolution sufficient to estimate final rock properties. The scanning equipment which is used for this process can provide the resolution required to provide sufficient detail in step (54). If sufficient detail cannot be achieved in step (54) despite many iterations through the process loop including steps (55), (58), and (51)-(54), a different kind of scanning system can be used on the samples to determine if sufficient detail can be achieved using a different kind of image scanner.

In step (56), final rock properties can be estimated once a suitable image is obtained as determined in step (54). Final rock properties to be estimated, for example, can include: porosity (e.g., connected, isolated, total), organic matter content, absolute permeability in multiple axes (e.g., x,y,z), grain size distribution, elastic properties (e.g., compression sound velocity, shear sound velocity, Young's modulus, bulk modulus, shear modulus, Poisson's ratio), formation factor, relative permeability: two-phase relative permeability (e.g., water-oil, gas-oil, or water-gas displacement), capillary pressure (e.g., capillary pressure values at each saturation for primary drainage, imbibition, and secondary drainage cycles), Archie's parameters m and n, or any combinations thereof. In step (57), final rock properties from all or part of the samples and sub-samples can be upscaled to provide a comprehensive assessment of the rock properties for the original sample. Results from multiple samples can be combined to provide an assessment of the rock properties of a facies or formation.

Figure 3:
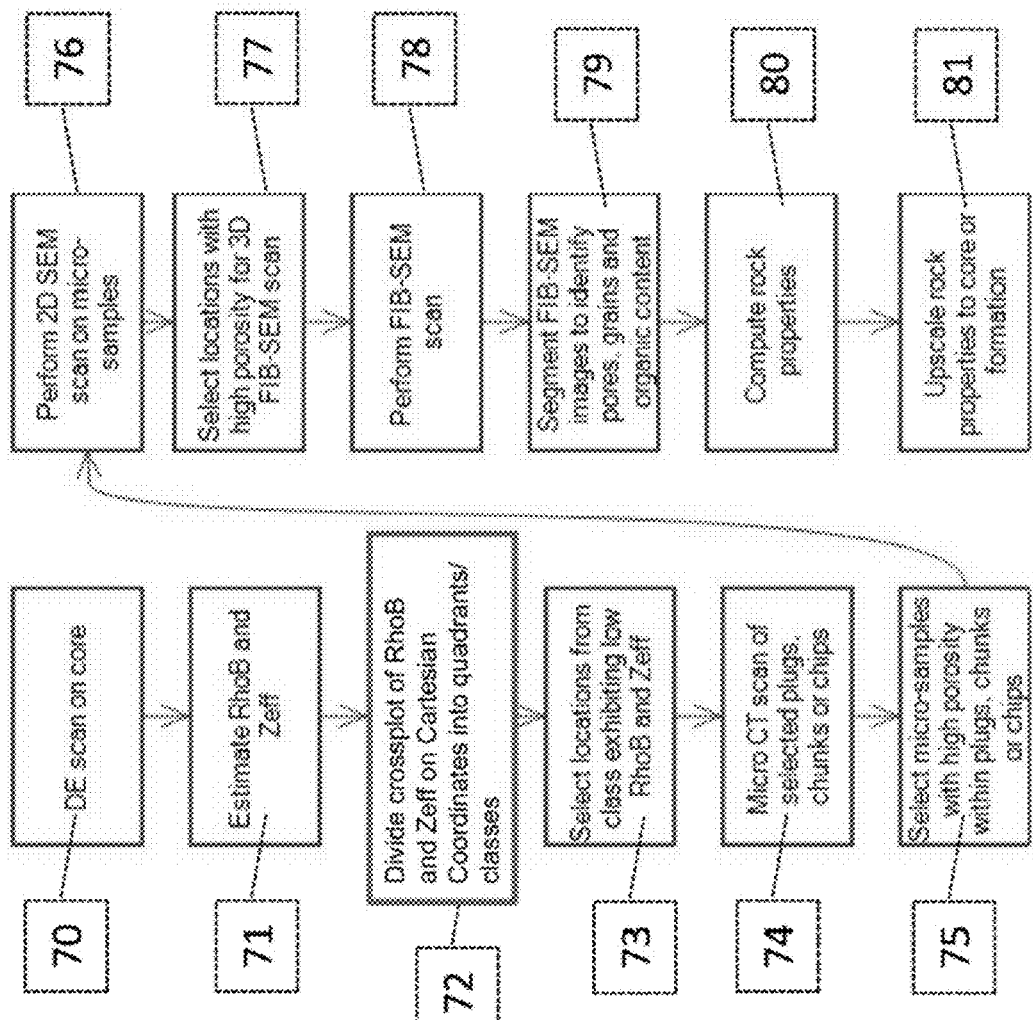
FIG. 3 is a flow chart describing a method applicable to porous rock such as shale, wherein this method employs a micro CT X-ray scanner, according to an example of the present invention.

Referring to FIG. 3, a method according to another example of the present invention is provided. The method can begin with a sample of a porous medium, such as a shale sample, that is large relative to the pore structure of the porous medium. A well core is an example of one such sample. Drill cuttings or similar samples of porous media also can be used. In step (70), the well core in this case is scanned with a low-resolution device, such as a dual energy X-ray CT scanner (DE scan). Wellington et al. shows that the attenuation of X-rays depends upon both electron density (bulk density) and effective atomic number. In step (71), this effect can be used in a method of the present invention to estimate rock properties, such as bulk density, RhoB, and effective atomic number, $Z_{eff}$, of digital slices along the length of the well core.

U.S. Patent Application No. 61/511,600, published as U.S. Patent Application No. 2013/0028371 A1, which is incorporated herein in its entirety by reference, describes methods which can be used herein to calculate RhoB and $Z_{eff}$ from high and low energy CT values. The method for estimating the bulk of at least one target object can involve, for example, one or more of the following steps which can be performed once or multiple times:

i. utilizing a scan (such as a dual energy X-ray CT scan) of reference objects with known bulk density and calibration objects with known bulk density and effective atomic number, ii. obtaining a functional relationship between bulk density error and effective atomic number using scan values (e.g., CT values) from the reference objects and the calibration objects, iii. utilizing a scan (such as a dual energy X-ray CT scan) of the target object and the three or more calibration objects, iv. obtaining uncorrected density (e.g., RhoB or $\rho_C^T$) and effective atomic number (e.g., $Z_{eff}$ or $Z^T$) for the target object, v. obtaining bulk density corrections using the functional relationship between bulk density error and effective atomic number, and the effective atomic number, $Z_{eff}$ or $Z^T$, for the target object, and vi. obtaining the corrected bulk density using the bulk density corrections.

Figure 12:
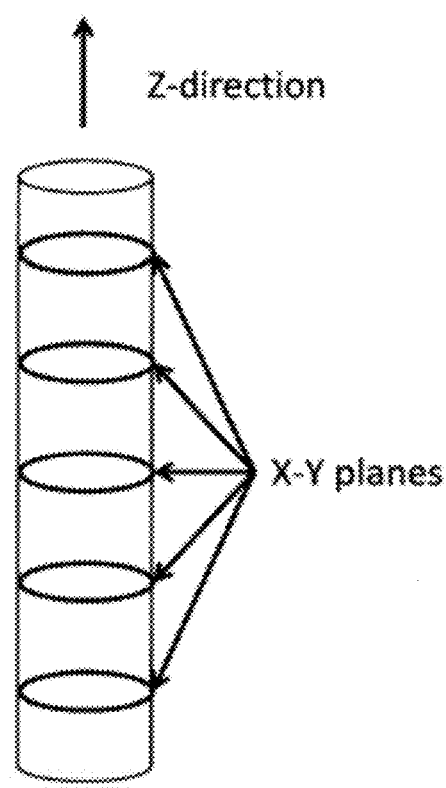
FIG. 12 is a perspective view of a core sample and the coordinate system used to reference the core.

Specifically, the method for estimating density and effective atomic number of a target object sample can comprise the following steps (steps I and II may be performed in any order):

I. Calculate a functional relationship between bulk density error and effective atomic number as follows:

i. Acquire a set of at least five objects with known density. At least two of these known objects match the scan geometry (target object size) and are designated as the reference objects and have different densities and chemical composition. At least three of the five objects are designated as calibration objects, and are generally homogeneous and made of materials with known and different densities and effective atomic numbers. The calibration objects must be at least as long as the reference objects and target objects such that the calibration objects are always in the field of the X-rays when the target object or reference objects are in the field of the X-rays. Reference objects, as used here, can refer to whole cores, fragments of whole cores, or objects manufactured for this purpose. The density and effective atomic number values of the reference objects should cover the expected range of densities and effective atomic numbers in the target object under investigation.

ii. Calculate the uncorrected density, RhoB or P and effective atomic number, $Z_{eff}$ or $Z^R$, for the reference objects as follows.

a. The reference objects and calibration objects are simultaneously imaged in an X-ray CT scanner.

b. Record the high CT value, $CTH_V^R$, and low CT value, $CTL_V^R$, for each voxel in the reference objects. In the case of cores, the core axis is aligned with the Z axis of the image (see FIG. 12).

c. Record the high CT value, CTH, and the low CT value, CTL, for each voxel of each of the calibration objects, $CTH_V^C$ and $CTL_V^C$, and average them over all of the voxels in each X-Y plane of each of the calibration objects, $CTH_{X-Y}^C$ and $CTL_{X-Y}^C$.

d. Use the known bulk density, $\rho_0^C$, and effective atomic number, $Z_0^C$, of at least three of the calibration objects and their respective CT values, $CTH_{X-Y}^C$ and $CTL_{X-Y}^C$, to solve the system of equations (8, 9)

$$\rho_0^C = A*CTH_{X-Y}^C + B*CTL_{X-Y}^C + C \quad (8)$$

$$\rho_0^C(Z_0^C)^\alpha = D*CTH_{X-Y}^C + E*CTL_{X-Y}^C + F \quad (9)$$

for coefficients A, B, C, D, E, F. The value of the exponent α may be 2.98, 3.6, 3.8, 4.0 or other values. For rock samples a value of α=3.8 is preferred. If the system of equations is over-specified, a least squares or other method may be used to determine the best or optimum values of the coefficients A, B, C, D, E, F.

e. Using $CTH_V^R$, and $CTL_V^R$ values from the reference objects and coefficients (A, B, C, D, E, F) from step I-ii-d above, calculate the reference objects' density and effective atomic number for each voxel in the reference objects, $\rho_V^R$ and $Z_V^R$, from equations (10, 11)

$$\rho_V^R = A*CTH_V^R + B*CTL_V^R + C \quad (10)$$

$$\rho_V^R(Z_V^R)^\alpha = D*CTH_V^R + E*CTL_V^R + F \quad (11).$$

iii. For each reference object, n, average the values of $\rho_V^R$ and $Z_{avg}^R$. The averages, $\rho_{avg}^R$ and $Z_{avg}^R$, are calculated. The averaging can be performed over the whole volume of the reference object, or over a selected portion of it, free of the boundary effects of the scan. The preferred method is to average the CT values for each slice in the reference object, n, and then calculate bulk density and effective atomic number for each slice directly from the average CT values, and then average the density and effective atomic number of slices.

iv. For each reference object, n, measure its mass and volume and calculate the measured average bulk density, $\rho_0^R$, as a ratio of mass over volume.

v. For each reference object, n, compute the absolute error in density, δ, and the relative error in density, ε, from $$\delta = \rho_{avg}^R - \rho_0^R \quad (12)$$

$$\varepsilon = \frac{\rho_{avg}^R - \rho_0^R}{\rho_0^R}. \quad (13)$$

vi. Determine a functional relationship between ε and the effective atomic number, Z, by solving the following system of equations (14) for a and b $$\varepsilon(1) = a*Z_{avg}^R(1) + b \quad (14a)$$

$$\varepsilon(2) = a*Z_{avg}^R(2) + b \quad (14b)$$

$$\varepsilon(n) = a*Z_{avg}^R(n) + b \quad (14c)$$

where ε(n)=relative error of density for reference object n, $Z_{avg}^R$ (n)=calculated average effective atomic number for reference object n, a and b are constants.

If the system of equations (14) is over-specified, a least squares or other method may be used to determine the best or optimum values of the coefficients a and b.

vii. Determine a functional relationship between δ and the effective atomic number, Z, by solving the following system of equations (15) for a and b $$\delta(1) = c*Z_{avg}^R(1) + d \quad (15a)$$

$$\delta(2) = c*Z_{avg}^R(2) + d \quad (15b)$$

$$\delta(n) = c*Z_{avg}^R(n) + d \quad (15c)$$

where δ(n)=relative error of density for reference object n, $Z_{avg}^R$(n)=calculated average effective atomic number for reference object n, a and b are constants.

If the system of equations (15) is over-specified, a least squares or other method may be used to determine the best or optimum values of the coefficients c and d.

II. Calculate the uncorrected density, $\rho_C^T$, and effective atomic number, $Z^T$, for the target object as follows:

i. The target object and calibration objects are simultaneously imaged in an X-ray CT scanner. The calibration objects used here are the same calibration objects as used in I-i above. In the case of cores, the core axis is aligned with the Z axis of the image (see FIG. 12).

ii. Record the high CT value, $CTH_v^T$, and low CT value, $CTL_v^T$, for each voxel in the target object. In the case of cores, the core axis is aligned with the Z axis of the image (see FIG. 12).

iii. Record the high CT value, $CTH_v^C$, and the low CT value, $CTL_v^C$, for each voxel of each of the calibration objects and average them over all of the voxels in each X-Y plane of each of the calibration objects, $CTH_{X-Y}^C$ and $CTL_{X-Y}^C$.

iv. Use the known bulk density, $\rho_0^C$, and effective atomic number, $Z_0^C$, of the calibration objects and the CT values $CTH_{X-Y}^C$ and $CTL_{X-Y}^C$ to solve the system of equations (16, 17) in each X-Y plane of the scan:

$$\rho_0^C = G*CTH_{X-Y}^C + H*CTL_{X-Y}^C + J \quad (16)$$

$$\rho_0^C(Z_0^C)^a = K*CTH_{X-Y}^C + L*CTL_{X-Y}^C + M \quad (17)$$

for coefficients G, H, J, K, L, M. If the system of equations is over-specified, a least squares or other method may be used to determine the best or optimum values of the coefficients G, H, J, K, L, M.

v. Use CT values from the target object, $CTH_v^T$, and $CTL_v^T$, and coefficients (G, H, J, K, L, M) from step II-iv above, to calculate the target object's density, $\rho_v^T$, and effective atomic number, $Z_v^T$, for each voxel in the target object, from equations (18, 19):

$$\rho_v^T = G*CTH_v^T + H*CTL_v^T + J \quad (18)$$

$$\rho_v^T(Z_v^T)^a = D*CTH_v^R + E*CTL_v^R + F \quad (19).$$

III. For each voxel in the target object, calculate the relative error in density, $\epsilon_v^T$, from equation (20)

$$\epsilon_v^T = a*Z_v^T + b \quad (20)$$

where a and b are coefficients calculated from step I-vi above.

IV. For each voxel in the target object, calculate the absolute error in density, $\delta_v^T$, from equation (21)

$$\delta_v^T = c*Z_v^T + d \quad (21)$$

where c and d are coefficients calculated from step I-vii above.

V. Calculate corrected bulk density values, $\rho_v^{T\epsilon}$, by applying the relative error correction factors, $\epsilon_v^T$, to the calculated density values, $\rho_v^T$, using equation (22):

$$\rho_v^{T\epsilon} = \frac{\rho_v^T}{1+\epsilon_v^T}. \quad (22)$$

VI. Calculate corrected bulk density values, $\rho_v^{T\delta}$, by applying the absolute error correction factors, $\delta_v^T$, to the calculated density values, $\rho_v^T$, using equation (23):

$$\rho_v^{T\delta} = \rho_v^T - \delta_v^T \quad (23).$$

VII. Either $\rho_v^{T\epsilon}$ or $\rho_v^{T\delta}$ may be used as an improved estimate of bulk density based on choosing the model giving the least average error in bulk density.

VIII. Optionally, either $\rho_v^{T\epsilon}$ or $\rho_v^{T\delta}$ may be averaged over the voxels in each X-Y plane of the target object to produce a bulk density log.

IX. Optionally, $Z_v^T$ may be averaged over the voxels in each X-Y plane of the target object to produce an effective atomic number log.

X. Optionally, either $\rho_v^{T\epsilon}$ or $\rho_v^{T\delta}$ may be averaged over all the voxels in the entire target object to produce an average bulk density for the entire target object.

XI. Optionally, both $\rho_v^{T\epsilon}$ or $\rho_v^{T\delta}$ may be averaged using simple or weighted averages to produce density logs or average bulk density values.

XII. Optionally, calculate the standard deviation, $\sigma_\epsilon$, of the differences between the average corrected calculated bulk density using relative error correction and the average physically measured bulk density, $\rho_{avg}^{R\epsilon} - \rho_0^R$, for every reference object. Calculate the standard deviation, $\sigma_\delta$, of the differences between average corrected calculated bulk density using absolute error correction and the average physically measured bulk density, $\rho_{avg}^{R\delta} - \rho_0^R$, for every reference object. The correction method, absolute or relative, with the lowest standard deviation, $\sigma^\epsilon$ or $\sigma_\delta$, is used to estimate the corrected bulk density of the target object.

Areas of great interest to geologists or petroleum engineers in rock samples such as shales, can be those areas where organic material, such as kerogen, and sufficient porosity are both present. In step (72), these areas of interest can be identified, for example, by creating a cross plot of RhoB versus $Z_{eff}$ on Cartesian coordinates. In step (72), for example, the crossplot is divided into four or more quadrants. Gardner, J. S., et al., "LITHO-DENSITY*LOG INTERPRETATION," SPWLA Twenty-First Annual Logging Symposium, Jul. 8-11, 1980, pp. 1-23, shows a $P_e$ (apparent photoelectric absorption cross section) measurement used in combination with density to analyze two-mineral matrices and to determine porosity, and in combination with density and neutron (φN) to analyze more complex lithologies which calls for more complex computations and crossplot analysis. Such concepts can be adapted for use in the present application. Atomic number (Zeff), photoelectric absorption, or both, can be related to a rock matrix in methods of the present application. Crossplots of RhoB versus $P_e$, for example, can be used in a method of the present application.

Figure 4:
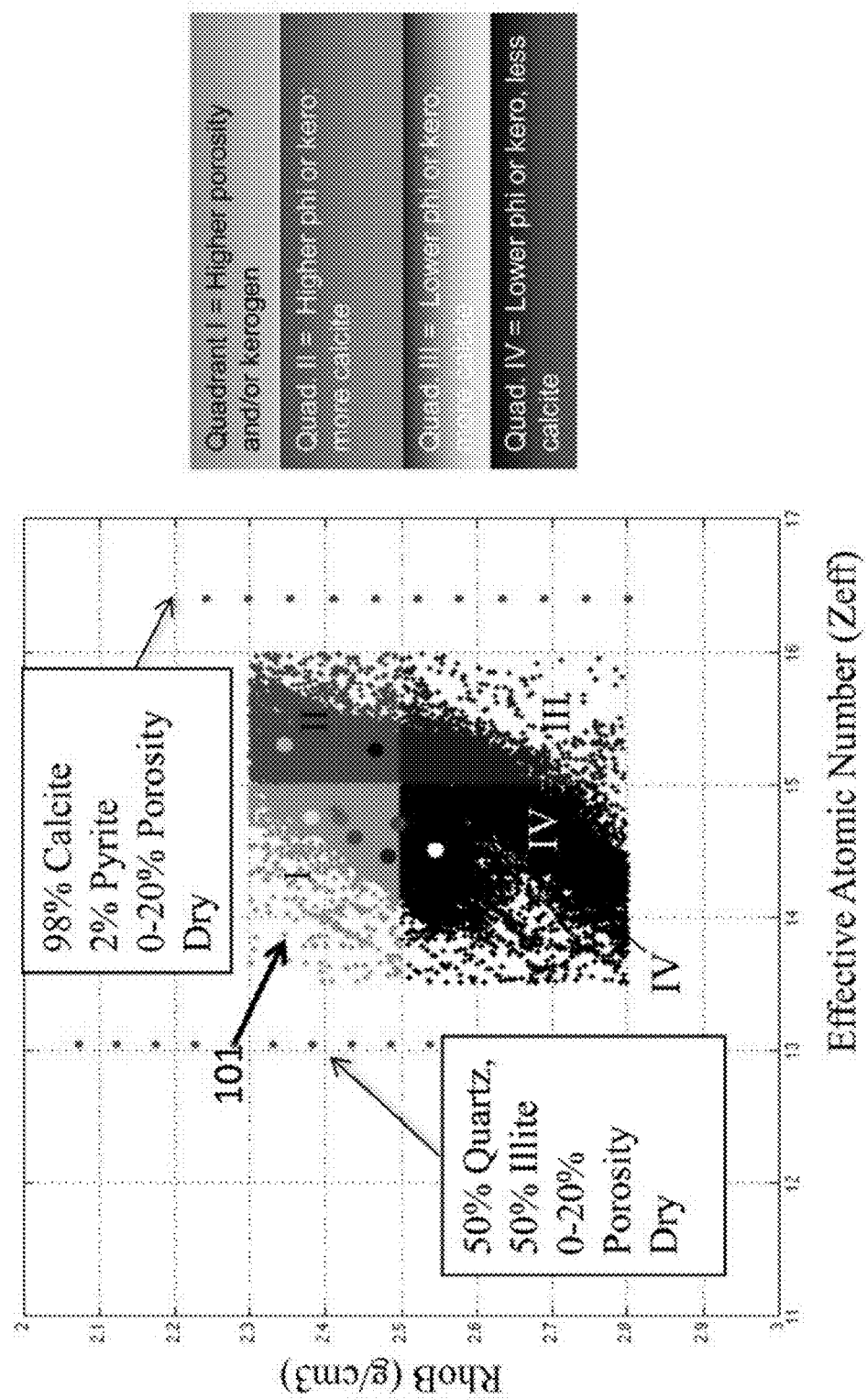
FIG. 4 is a plot of bulk density and effective atomic number for sub-samples in a porous medium used to identify sections of the sample of a porous medium in a method according to an example of the present invention.

Step (72) of FIG. 3 can be further understood with reference to the illustrative plot provided in FIG. 4. FIG. 4, for example, shows a RhoB versus $Z_{eff}$ cross plot (101) on Cartesian coordinates created for a shale sample. As shown in FIG. 4, for example, the data pairs of cross plot (101) can be separated into four quadrants (e.g., I, II, III, and IV). Quadrants are defined based on geological formation information from where the sample originated from. The circles shown in FIG. 4 are the selected plug locations from Rhob and Atomic Number from the whole core). In general, regions or quadrants of the core with lower values of RhoB and lower values of $Z_{eff}$ relative to other regions and quadrants thereof are considered to be likely areas of higher porosity (ø or "phi") and organic matter respectively. For example, with reference to the plot of FIG. 4, Quadrant IV is a region with higher values of RhoB and lower values of $Z_{eff}$, whereas Quadrant I has comparatively lower values of RhoB, Quadrant II has comparatively lower values of RhoB and higher values of $Z_{eff}$, and Quadrant III has comparatively higher values of $Z_{eff}$. Other selected combinations of RhoB and $Z_{eff}$ can be considered to locate regions of the sample for further analysis. For example, if it is desired to locate regions of the sample that are porous and brittle, then low values of RhoB with high values of $Z_{eff}$ can be selected, such as Quadrant II in FIG. 4. If it is desired to find locations in the sample that are porous and consist primarily of quartz, then low values of RhoB combined with $Z_{eff}$ values typical of quartz can be selected, such as Quadrant I in FIG. 4. In the case where high organic matter content is of interest, for example, the data on data slices in the top left quadrant (I) of the RhoB versus $Z_{eff}$ plot (101) in FIG. 4 can be selected for further analysis because areas with relatively low RhoB and relatively low $Z_{eff}$ typically contain higher concentrations of organic matter and/or porosity. In FIG. 4, "kero" refers to kerogen. Other combinations of RhoB and $Z_{eff}$ can be used depending upon the combination of rock properties that are indicative of areas or volumes of interest.

Figure 5:
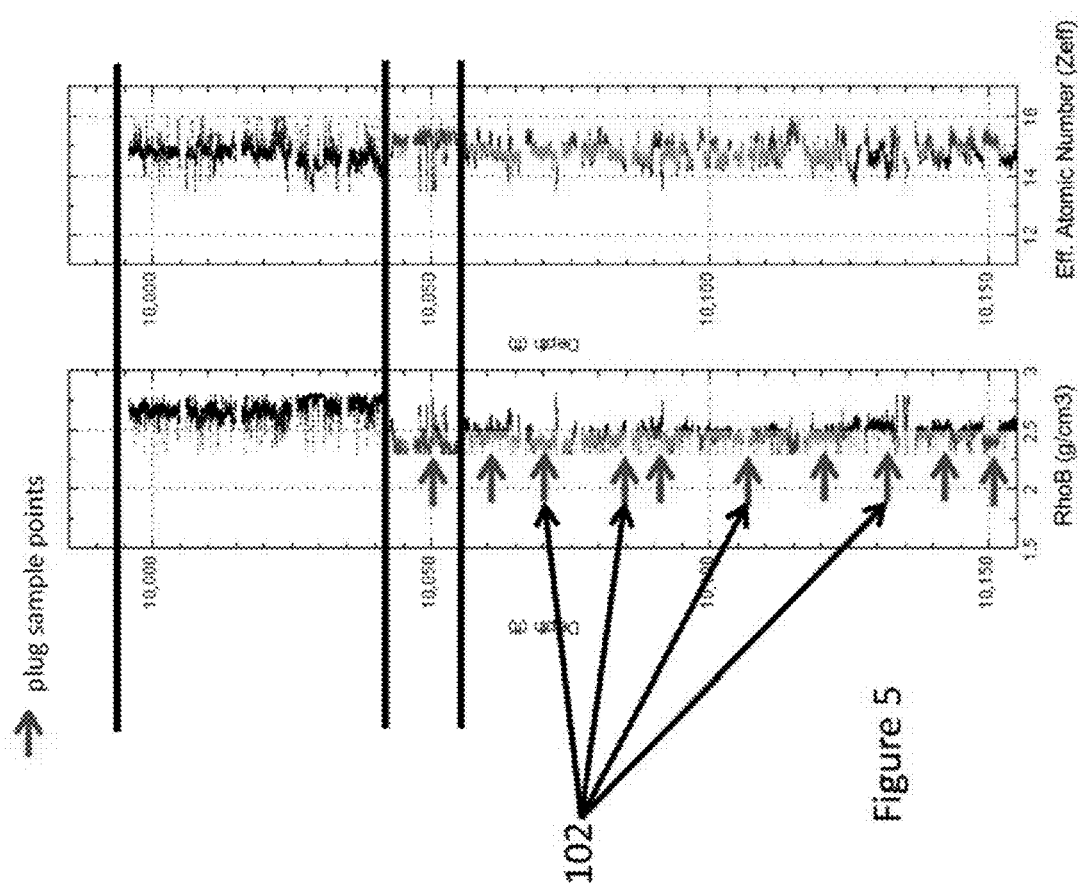
FIG. 5 is a log of bulk density RhoB (g/cm$^3$) and effective atomic number ($Z_{eff}$) with respect to well depth for sub-samples in a porous medium used to identify sections of the sample of a porous medium, according to an example of the present invention.

In step (73) of the method shown in FIG. 3, selected core locations from the left top quadrant (I) of the RhoB versus $Z_{eff}$ plot of FIG. 4 can be selected for plug samples. Sample chips or chunks can be used in lieu of plugs. The plugs, chips or chunks can be roughly cylindrical in shape, and can have a length of 1 cm to 5 cm and a diameter of 2 cm to 4 cm. Other sizes outside of these ranges can be used. FIG. 5 shows a log of the RhoB and $Z_{eff}$ data pairs of this example with respect to well depth. The arrows (102) in FIG. 5 indicate locations in the core where plug samples are taken for further analysis. The linear distance between plugs, chips or chunks along the length of the core typically can be 3-9 feet, or other intervals. The interval between chips, chunks or plugs can be varied depending upon the thickness of the facies being evaluated. The interval between chips, chunks or plugs can be increased to cover a greater range of the subterranean formation but some valuable data points may be missed. A decision is made to balance the time and cost required for more data points with the expected added value of more data points.

In step (74) of FIG. 3, the selected plug samples can be scanned at higher resolution with a Micro CT X-ray scanner to produce a digital representation of the pore, grains and organic content of the selected plugs. The Micro CT X-ray scanner can have a resolution from 0.5 um to 100 um. Areas of high porosity, specific mineral content, or other characteristics may be identified by inspection or, optionally, the voxels produced from this higher resolution scan area segmented to classify each voxel as grain or pore. This segmentation can be accomplished if the Micro CT X-ray scan has sufficient resolution to identify a majority of the pores in the sample. Segmentation can be accomplished, for example, by methods such as described by Nur (U.S. Pat. No. 6,516,080), which is incorporated herein in its entirety by reference, or as described by Knackstedt et al (Digital Core Laboratory: Properties of Reservoir Core Derived from 3D Images, Society of Petroleum Engineers Asia Pacific Conference, 2004), or other suitable segmentation method.

In the case where high organic matter content is of interest, locations within each plug, core or chip that have relatively high porosity or have relatively low RhoB and $Z_{eff}$ can be selected for further analysis. The areas of relatively high porosity or relatively low RhoB and $Z_{eff}$ can be the region of interest of samples from the original sample that are likely to contain organic matter. In step (75), samples can be taken from the areas of relatively high porosity, if a Micro CT X-ray scan is used. Samples selected are typically tiles. The tiles can be mechanically cut from slices taken from the plug, chip or chunk at selected locations. The average size of the tiles can be from 2 mm×2 mm×400 μm to 6 mm×6 mm×500 μm. Typically 1 to 5 samples can be selected from each plug. After being cut, samples can be mechanically polished and a final ion beam polishing can be performed using an ion polisher or similar device. The surface of the tiles should be sufficiently smooth such that a clear image can be produced from a scanning electron microscope (SEM).

Figure 6:
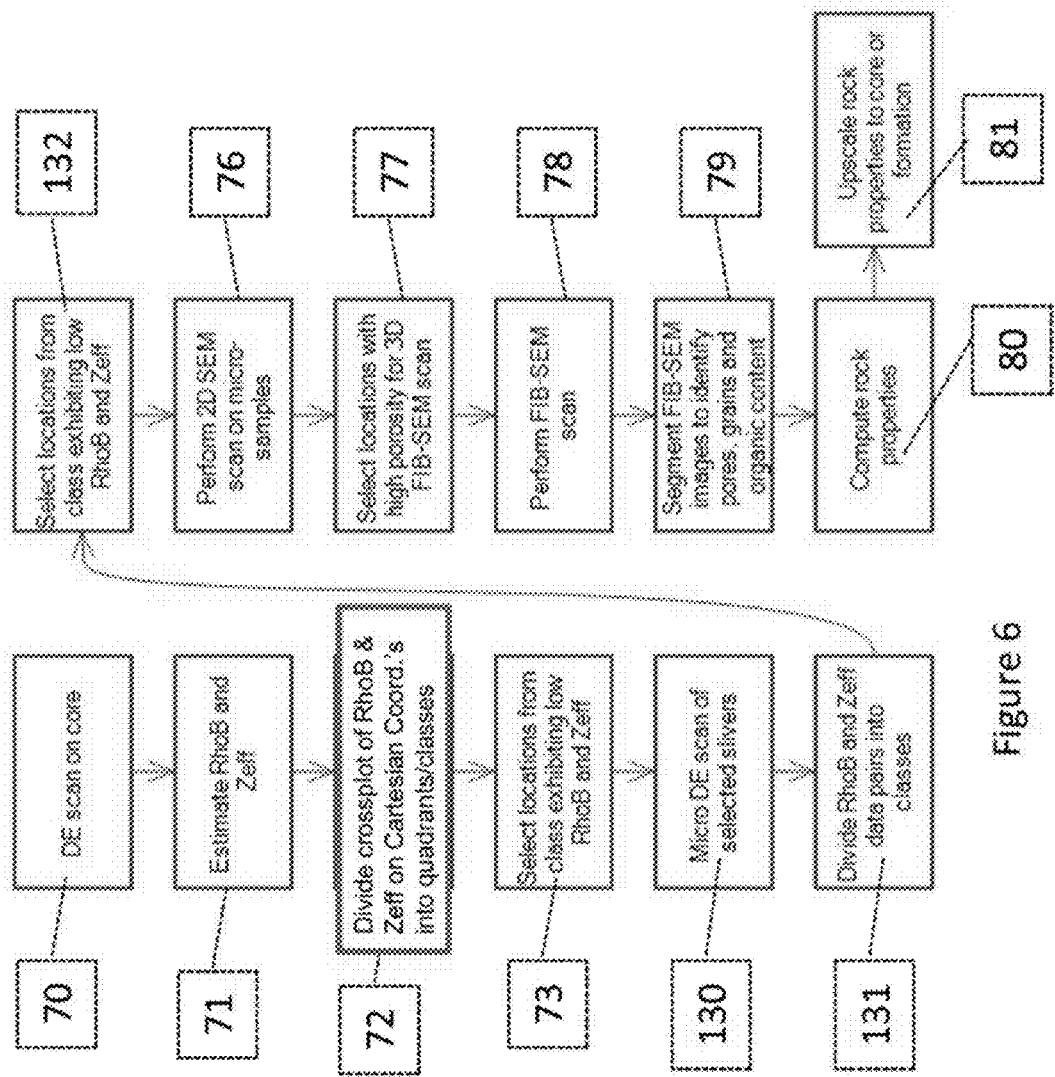
FIG. 6 is a flow chart describing a method applicable to porous rock such as shale, wherein this method employs a dual energy micro CT X-ray scanner, according to an example of the present invention.

Optionally, a dual energy Micro X-ray projection can be performed on the plug, chip, or chunk using a MicroCT 100 manufactured by Xradia Corporation or similar instrument. For example, the method shown in FIG. 3 can be modified according to an example of the present invention wherein steps (74) and (75) thereof are replaced by steps (130), (131), and (132) such as shown in FIG. 6. This alternative method shown in FIG. 6 can be a preferred method when the pores in the sample are small and cannot be resolved by the Micro CT X-ray scan. Referring to step (130) in FIG. 6, for example, the dual energy Micro X-ray projection can be done in a similar manner to the dual energy CT X-ray scan. In step (131) of FIG. 6, RhoB and $Z_{eff}$ can be estimated for each region in the sample and RhoB-$Z_{eff}$ data pairs can be plotted in a similar manner as indicated for step (72) of FIG. 3, and reference is made thereto. In step (132) of FIG. 6, locations with relatively low values of RhoB and $Z_{eff}$ can be selected for sampling in a similar manner to location selection from the core sample, such as described herein with respect to step (73) of the method of FIG. 3. As described above, alternate combinations of RhoB and $Z_{eff}$ can be selected if regions with other characteristics are of interest. Further, although steps 71-73 in FIGS. 3 and 6 illustrate the method using atomic number (Zeff values), the atomic number can be converted to photoelectric absorption cross section ($P_e$), and $P_e$ can be used in methods of the present application. Photoelectric absorption alternatively may be referred to as photoelectric effect index ("PEF"). $P_e$ (or PEF) may be calculated from atomic number (Zeff) by the equation: $P_e=(Z_{Eff}/10)^{3.6}$. Crossplots of RhoB and $P_e$ (or PEF) on Cartesian coordinates, for example, can be generated and used in methods of the present application, such as in a similar manner as shown herein for the crossplots of RhoB and Zeff.

Steps (76)-(81) of the methods shown in FIGS. 3 and 6 herein can be the same and are commonly discussed hereafter. The selected samples in step (75) of the method illustrated in FIG. 3, or the selected sample locations of step (132) of FIG. 4, as applicable, can be imaged in step (76) with an SEM at higher resolution than the Micro CT X-ray scan or the dual energy Micro CT X-ray scan, as applicable. The higher resolution of the SEM imaging can be, for example, such as from about 5 nanometers to about 30 nanometers, or larger. An SEM or SEM with energy dispersive spectral analysis (EDS) capability can be used to make 2D scans at nominally 20 nanometer resolution. EDS is an analytical technique used for the elemental analysis or chemical characterization of a sample. The EDS spectrum can comprise estimates of rock materials, such as clay, pores, organic matter, calcite, quartz, plagioclase, pyrite, titanium dioxide, and estimates of similar materials and combinations thereof. The SEM image with EDS can be used to identify the pores, mineralogy and organic content of the sample. FIG. 7a is an SEM image of a sample from Eagle Ford shale (South Texas). FIG. 7b is an X-ray spectral map showing different colors, which correspond to different minerals present in the sample. FIG. 7c is a table showing the volume percent distribution of pore, organic material and various minerals in the sample. Organic material is typically kerogen that is present inside the pores of the sample. FIG. 8 is a ternary diagram illustrating the distribution of interparticle pores 111, intraparticle pores 112, and organic matter pores 110 in a porous rock sample, with reference made to Loucks, R. G., et al.; Preliminary Classification of Matrix Pores in Mudrocks, presented to Gulf Coast Association of Geological Societies (GCAGS), April, 2010, incorporated in its entirety by reference herein.

In step 77 of FIG. 6, samples (tiles) from the 2D scan with relatively high organic matter content and porosity can be selected for 3D analysis at higher resolution than the 2D scan. Resolutions of 5 to 15 nanometers can be used for 3D scans of a typical shale sample. The equipment used for the 3D scan can be, for example, a Focused Ion Beam-Scanning Electron Microscope (FIB-SEM). In step 78, multiple 2D images are produced with the FIB-SEM scanning. Two images, an SE-2 image and an ESB image (BSE-1), can be produced from each 2D scan. For example, physical locations of regions of interest of pixels from the 2D digital images created using the SEM with EDS capability can be imaged using SE-2 and ESB detectors with a nominal resolution of 5 to 15 nanometers and a field of view of 5,000×5,000 nanometers to 30,000×30,000 nanometers. A layer of the sample then can be removed (milled) with the focused ion beam and the sample can be scanned again producing SE-2 and ESB images. The thickness of the milled layer can be from about 5 nm to about 20 nm. The SE-2 and ESB images provide differing data on pores and organic matter. Another layer then can be removed and another pair of SE-2 and ESB images can be produced in the SEM. The process of removing a layer and scanning the SEM can be repeated to accumulate, for example, 500 to 800 2D images. The multiple 2D images can be aligned to produce a 3D image that then can be segmented, such as indicated in step (79), to classify each voxel in the 3D image as mineral, organic matter or pore.

A method and system such as described by Carpio et al in U.S. Provisional Patent Application No. 61/547,095, which is incorporated herein in its entirety by reference, or similar method and systems can be used to segment the 3D image. For example, dual signals can be simultaneously acquired with an SE2 detector and ESB detector that are used with the FIB-SEM device. Image data is recorded based on the detected surface electrons of the sample and stored as a two-dimensional image comprising a value of gray scale allocated to each of a plurality of pixels in the images. A separate set of image data is recorded based on the detected backscattered electrons emitted by the sample during the scanning and stored as two-dimensional images comprising a value of gray scale allocated to each of a plurality of pixels in the images. The two-dimensional images provide a dual set of image data associated with the scanned sample. The two-dimensional images obtained based on dual surface electron and backscatter electron detection each can be stacked and aligned in the previously mentioned manner or manners. The dual sets of image data can then be analyzed to allocate pixels in the gray scale images to pore space, organic matter, or mineral to form the base analyzed images. Routines can be provided which use the ESB (BSE-1) data as a second image set to enhance the accuracy of the labeled pore and organic matter phases in the SE2 data as a primary image set. Two masks are created from the ESB data for two purposes. As one purpose, organic matter is re-labeled as pore in locations where material inside the pore from a deeper slice appears in the organic matter gray scale range. Close inspection of ESB data, which is taken simultaneously with and aligned to the SE2 data, reveals that in areas which pore has been mislabeled as organic matter, the ESB data has a significantly higher gray scale value than areas labeled as organic matter that are correct. As indicated, this difference is exploited to correct the porosity mislabeled as organic matter while leaving real organic matter unaffected. As another purpose, mineral is re-labeled as organic matter in locations where the organic matter has charged into the gray scale range of mineral during scanning, such as by a FIB-SEM device. As indicated, the same ESB data set used to correct the porosity can be used to correct the organic matter, wherein the segmented mineral phase that should be organic matter has a significantly lower gray scale value in the ESB data set than areas labeled as mineral that are correct. Organic matter mislabeled as mineral in the surface electron data is corrected while leaving real mineral unaffected.

Once the segmented images have been produced, rock properties can be computed, such as indicated in step (80). For example, Routine Core Analysis (RCAL) and Special Core Analysis (SCAL) can be completed using digital rock physics methods. RCAL analysis includes but is not limited to porosity (connected, isolated, total), organic matter content, absolute permeability in multiple axes (x,y,z), grain size distribution, elastic properties, and formation factor. SCAL analysis includes but is not limited to relative permeability, capillary pressure, Archie's parameters m and n, and similar analyses.

The RCAL and SCAL rock properties determined as above can be upscaled, such as indicated in step (81), to either the well core level or formation level. Upscaling may be accomplished in a number of manners.

One method to upscale, for example, can be to sub-divide the digital image that was used for SCAL and RCAL calculations and repeat the computations. The resulting sub-samples can describe the variation within a larger sample, help determine a representative elementary volume of the sample, and define a relationship between physical properties like porosity and permeability. This relationship extends in general beyond the sample from which the subsamples were taken.

The upscaling can comprise sub-dividing the segmented 3D images into sub-images, estimating rock properties for each of the sub-image, establishing a best fit correlation between pairs of selected rock properties, and using the best fit correlation between pairs of selected rock properties to characterize the rock properties of the facies or formation from which the sample was taken.

Figure 9:
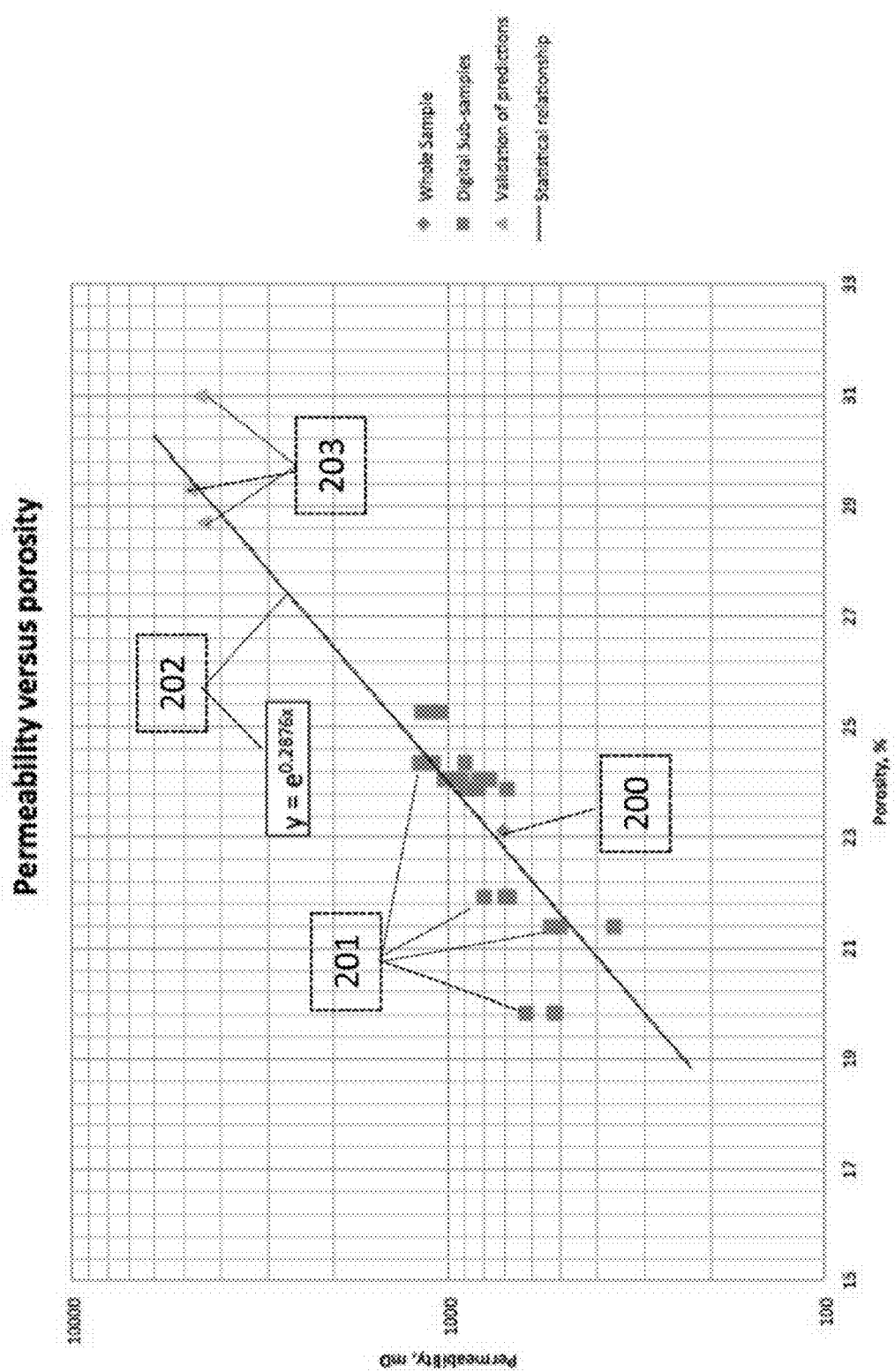
FIG. 9 illustrates a method of upscaling by sub-dividing a digital image according to an example of the present invention.

FIG. 9 is a plot of permeability versus porosity. The shaded diamond (200) is the estimated porosity and permeability of a sample of a carbonate rock as computed by digital rock physics analysis of an X-ray CT scan of the rock. The shaded squares (201) are the estimated permeability and porosity of 24 digital subsamples of the same rock (200). An equation (202) is created from a statistical fit of the data (201). The equation (202) can be extended beyond the range of permeability and porosity contained in the original sample. This extension upscales the original data to provide estimates of rock properties for other rocks of the same type as the original sample. The shaded triangles (203) are the permeability and porosity of three other samples from the same carbonate formation. The value of permeability and porosity of the samples (203) are significantly different than the original sample (200). However, the samples (203) fall generally on the trend line (202) defined by the relationship derived from the original subsamples.

The upscaling can comprise correlating selected pairs of estimated rock properties with physical locations on the indicated samples and/or subsamples, then assigning the remaining estimates of rock properties to corresponding sections of the samples and/or subsamples, and then using the assigned estimates of rock properties in a well simulation or reservoir simulation model.

Figure 10:
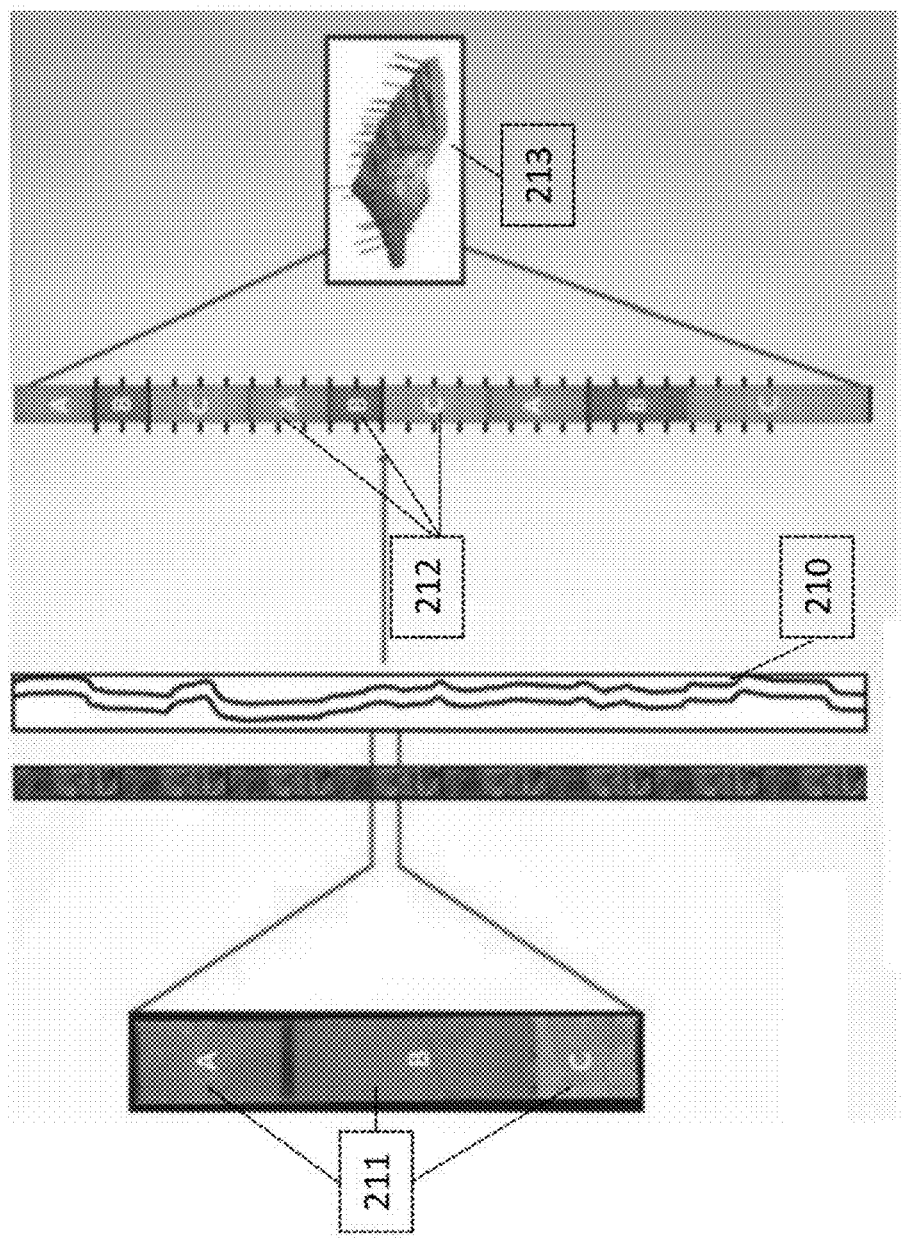
FIG. 10 illustrates a method of upscaling by assigning selected rock properties to sections of the rock sample, according to an example of the present invention.

FIG. 10 shows another method to upscale RCAL and SCAL estimates. In this example, a log of RhoB and $Z_{eff}$ values computed from the original dual energy scan of a core (210) can be examined and sections in the core with similar values or rock types (211) can be identified. In this example, there are three different rock types identified and labeled as A, B, and C on which RCAL and SCAL computations were completed. The core log then can be examined and sections of the core with rock types similar to the rock types identified in the original sample can be identified and mapped to the entire core (212). RCAL and SCAL for each rock type can be averaged across the core or used in a well model. This method of upscaling can be further extended to multiple cores taken from a formation. In this example, the rock types and associated RCAL and SCAL estimates can be mapped to multiple cores take from the formation (213). RCAL and SCAL information can be interpolated between multiple well cores to estimate properties of facies within a subterranean formation. The RCAL and SCAL estimates can also be used in a formation model.

Figure 11:
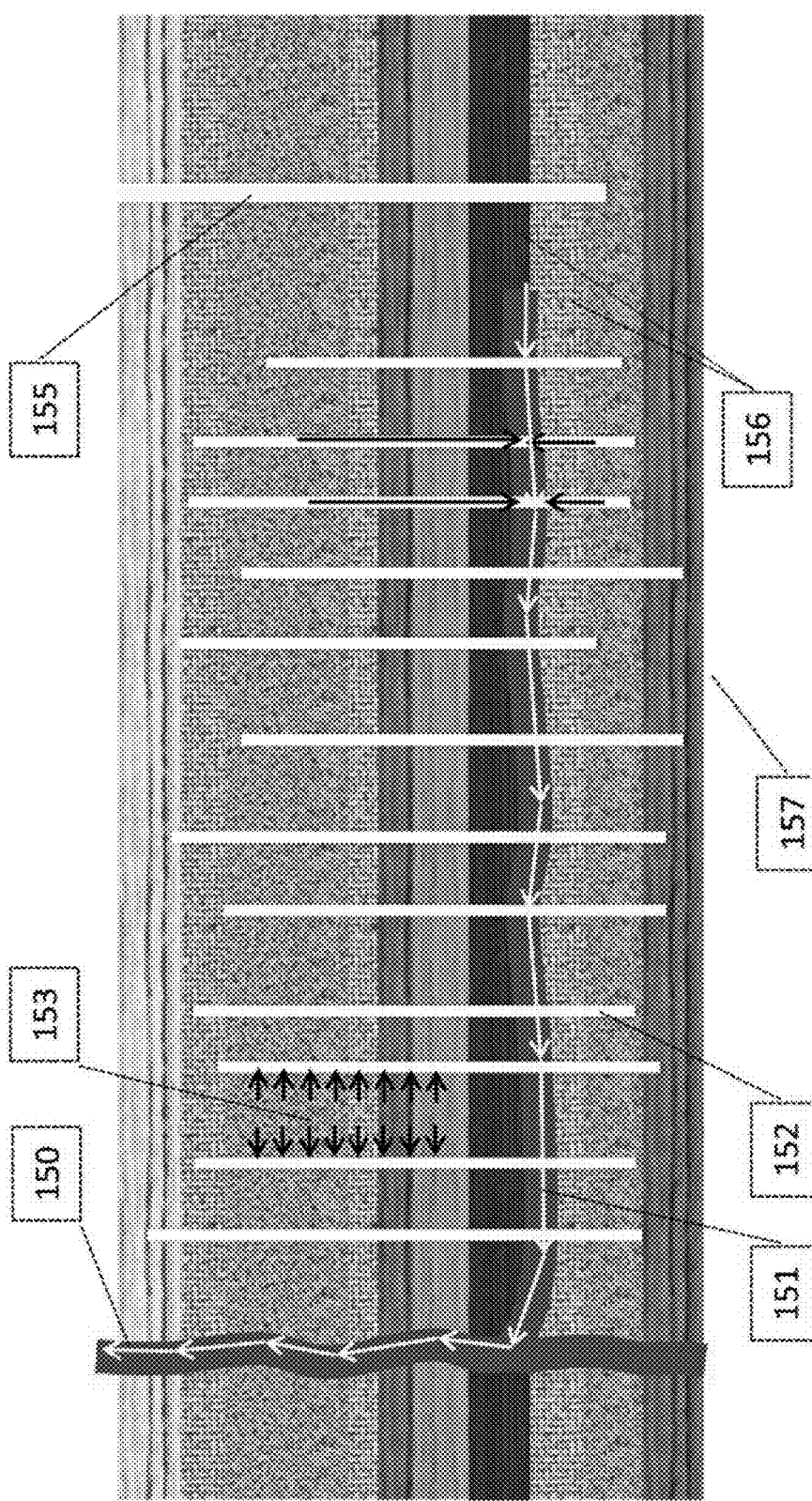
FIG. 11 is a diagram of a horizontal well, according to an example of the present invention.

Another method of upscaling in horizontal wells can be to use drill cuttings. The upscaling can comprise estimating rock properties of drill cuttings according to the method of the present invention and correlating the drill cuttings with the physical well location from which the drill cuttings were retrieved. A graphic of a well core (155) is shown in FIG. 11. Well cores are useful because they represent a vertical well bore (150) and provide information about the facies (156) that make up a subterranean formation (157). Many wells are horizontal wells (151). Typically, it is not possible to produce a well core from a horizontal well in the same manner that a vertical well core is produced. The present invention includes a method for obtaining information about the location and properties of facies within a subterranean formation by applying the methods above, such as shown diagrammatically in FIG. 3 and FIG. 6, to drill cuttings that are produced and recovered during the drilling operation.

Methods for obtaining and classifying drill cuttings in horizontal wells are described in U.S. Patent Application No. 61/535,601 (Ganz), which is incorporated herein in its entirety by reference. Drill cuttings can be extracted from a drilling fluid by means of a shale shaker or similar device. The drill cuttings can be classified and grouped based on the time they arrive at the surface. Drill cuttings can be grouped such that the downhole coordinates from which they were produced are estimated to be within about plus or minus 10 feet or more of actual. The grouped drill cuttings can be stored in a bag, canister or similar device for further processing. Optionally, the drill cuttings then can be further classified by size. For example, the fraction larger than 60 to 40 mesh or the fraction smaller than 40 to 60 mesh. Optionally, the drill cuttings can be cleaned by washing or similar process and dried. One or more groups of drill cuttings can be analyzed and the results arranged in sequential order. The corresponding downhole coordinates of the estimated location of the drill cuttings is recorded along with the physical location of the groups of drill cuttings. Optionally, the sequential arrangement of grouped drill cuttings can be placed in one or more containers. The container can be a tube with a circular, rectangular or other cross section. The container can be an open tray. The width of the container is selected such that the container and the contained drill cuttings can pass through the sample opening on an X-ray CT scanner or similar device. Optionally, the grouped, sequential drill cuttings can be secured by embedding them in a material to hold them securely in place. The material for this purpose may be a resin such as epoxy or similar material. Bulk density of the groups of drill cuttings can be physically measured. One method to do this would be to weigh a group of drill cuttings ($M_1$) and place them in a container of known volume ($V_1$). Then the container is filled with material which can fill the space in the container that is unoccupied by the cuttings but will not invade the pore space of the cuttings, and the volume of material required to fill the container is recorded ($V_2$). Bulk density ($\rho$) is then calculated, $$\rho = \frac{M_1}{V_1 - V_2}.$$

Also, cuttings can be weighed in air (w1), then weighed (w2) submerged in liquid such as oil or water (method of Archimedes). Bulk volume (BV) is (w1−w2)/fluid density, and RhoB is w1/BV. The grouped, sequential drill cuttings (the target object) then can be analyzed by a dual energy CT scan. As another method which can be used to obtain and classify drill cuttings in horizontal wells, a reconstituted core that comprises drill cuttings are grouped and classified according to the time at which they arrive at the surface transported by the drilling fluid. The groupings of drill cuttings that comprise the reconstituted core may or may not be physically assembled. The reconstituted core can be a physical assembly or a logical assembly. The reconstituted core cross-references the location on the reconstituted core and the subterranean location from which the drill cuttings were produced. The drill cuttings included in the reconstituted core can include the entire drill cuttings collected in a particular time period and from a particular subterranean location, or the drill cuttings may optionally be further classified according to size and/or shape. X-ray CT scans and estimates of bulk density and effective atomic number can be produced from the reconstituted cores, such as with methods described herein, which can be displayed graphically on paper similar to traditional well logs or they can be displayed electronically on a computer. The reconstituted core logs are effectively a log of the representation of a horizontal well core.

The present invention further comprises a system for implementing one or more of the methods as described above. The system can include an image scanner for a sample, such as a well core, plug, or cuttings, obtained from a formation, or sub-samples thereof.

The system can include, for example, a dual energy X-ray CT scanner. The dual energy X-ray CT scan can run at a resolution of 0.2 mm to 0.5 mm. The dual energy X-ray CT scanner creates measurements of radiodensity at two different energy levels that can be used to create an image from which estimates of RhoB and $Z_{eff}$ for each slice in the digital sample can be made. In general, regions of the core determined to have lower values of RhoB and lower values of $Z_{eff}$, such as with methods described herein, are likely areas for entrapment of organic matter. Sub-samples can be selected from those slices that have low combined estimates for RhoB and $Z_{eff}$.

The system further can include a micro CT X-ray scanner. The micro CT X-ray scanner can be used to create a three-dimensional representation of one or more selected sub-samples. The three dimensional representation can be used to estimate porosity, mineralogy, and other rock properties. In general, regions of the core with higher porosity are likely areas for entrapment of organic matter. Sub-samples can be selected from those sub-samples that have low porosity and mineralogy indicating the presence of organic compounds. Alternately, the micro CT X-ray scanner can be used to make a dual energy scan of one or more selected sub-samples. The data captured with the dual energy scan then can be used to estimate RhoB and $Z_{eff}$ for slices or subsections in each sub-sample. Slices or subsections with relatively low values of RhoB and $Z_{eff}$ can be potential areas containing high porosity and organic matter.

The system further can comprise equipment to prepare small samples of size suitable for SEM scanning. The sample preparation equipment can comprise equipment for cutting, milling or shaping devices to extract samples of porous media, and grinders, millers, polishers, or similar devices to prepare the surface of the porous media. Samples of approximately 4 mm×4 mm×500 µm are typical. Samples initially can be cut with a diamond tooth saw to a thickness of about 1 mm and then mechanically polished to a thickness of 400 µm-600 µm. Final polishing can be done with an ion polisher.

The system further can include a FIB-SEM with energy dispersive spectral analysis (EDS) capability. The SEM can be used to make 2D scans at nominally 65 nanometers to identify pore structure, mineralogy, and organic content of the sub-samples. A sub-set of the sub-samples then can be selected based upon those sub-samples exhibiting high porosity and organic content.

The system further can include a FIB-SEM with capability to detect both SE-2 and ESB electrons, and has ion milling capability. The FIB-SEM can be used to produce multiple images that can be segmented and assembled into a 3D representation of a rock sample.

The system further can comprise one or more computer systems (or computer programs stored on a non-transitory computer-readable medium) for processing images and computing rock properties. For example, the system or program can comprise one or more computer systems which can comprise software to capture images, process images, segment images, and/or estimate rock properties, or any combinations thereof. The image processing used in the present methods can be done with visualization and computation software. Segmentation techniques can also be used, such as those described for example in U.S. Pat. No. 6,516,080 (Nur) and U.S. Patent Application Publication No. 2009/0288880 (Wojcik, et al), which are incorporated herein in their entireties by reference. The segmentation method described in the above incorporated U.S. Provisional Application No. 61/547,090 (Carpio, et al) also can be used.

The system or program of the present invention can be located and used off-site or on-site with respect to where the samples are obtained. If used off-site, samples can be transported to the location where the system is located. If used on-site, the system optionally can be used in a mobile enclosure such as a trailer, van, motor coach or similar device, such that it can be transported to a well site and analyses run on-site.

The present invention also includes the following aspects/embodiments/features in any order and/or in any combination:

1. The present invention relates to a method for estimating selected physical properties of a rock sample, comprising:
   (a) preparing a rock sample,
   (b) creating a digital image of the rock sample by scanning the rock sample,
   (c) estimating selected physical properties of the rock sample from the digital image of the rock sample,
   (d) determining if the digital image provides sufficient detail for estimation of final rock properties, wherein step (e) directly follows step (d) if sufficient detail is not determined to be provided and step (j) directly follows if sufficient detail is determined to be provided,
   (e) identifying one or more regions within the rock sample that contain high porosity and/or organic matter content,
   (f) selecting subsamples of the rock sample that contain high porosity and/or organic content,
   (g) preparing rock subsamples from the selected subsamples,
   (h) increasing the resolution of the scanning of the rock sample,
   (i) repeating steps (b) through (d) until a desired resolution is achieved, and
   (j) estimating final rock properties.
2. The method of any preceding or following embodiment/feature/aspect, wherein the rock sample comprises organic mud rock, shale, carbonate, sandstone, limestone, dolostone, or any combinations thereof.
3. The method of any preceding or following embodiment/feature/aspect, wherein preparing the rock subsamples comprises cutting, abrading, shaping milling, focused ion beam polishing, or any combinations thereof.
4. The method of any preceding or following embodiment/feature/aspect, wherein the digital image comprises a two-dimensional (2D) image or a three-dimensional (3D) image.
5. The method of any preceding or following embodiment/feature/aspect, wherein creating a digital image of the rock sample by scanning the rock sample at a selected resolution comprises X-ray computed tomography, dual energy X-ray computed tomography, X-ray projection, scanning electron microscopy (SEM), focused ion beam scanning electron microscopy (FIB-SEM), or any combinations thereof.
6. The method of any preceding or following embodiment/feature/aspect, wherein physical properties of the rock sample comprise porosity, organic matter content, absolute permeability in at least one axis, relative permeability, two-phase relative permeability, capillary pressure, grain size distribution, electrical properties, elastic properties, or any combinations thereof.
7. A method for estimating selected physical properties of a rock sample, comprising:
   (a) acquiring a physical sample of a porous medium (Sample 1),
   (b) performing a dual energy X-ray CT scan of Sample 1,
   (c) creating 3D digital images (Image 1) of Sample 1 from the dual energy X-ray CT scan,
   (d) calculating the bulk density, RhoB, and effective atomic number, $Z_{eff}$, for each layer of voxels (Slices) in Image 1,
   (e) selecting a region of interest of the Slices of Image 1 comprising selected values of RhoB and $Z_{eff}$,
   (f) creating physical sub-samples (Sample 2) from selected Slices of Sample 1 wherein the Slices comprise selected values of RhoB and $Z_{eff}$,
   (g) scanning Sample 2 with a micro CT X-ray scanner or imaging Sample 2 using a micro X-ray projection,
   (h) creating 2D or 3D digital images (Image 2) of Sample 2,
   (i) calculating porosity or RhoB and $Z_{eff}$ of Image 2,
   (j) selecting regions of interest of pixels or voxels from Image 2 wherein such regions of interest have relatively high porosity or selected values of RhoB and $Z_{eff}$ (Image 2),
   (k) creating sub-samples (Sample 3) from the physical locations corresponding to Image 2,
   (l) preparing Sample 3 for SEM imaging,
   (m) creating 2D digital images (Image 3) of Sample 3 using an SEM or SEM with EDS capability,
   (n) estimating porosity of Image 3, and
   (o) estimating organic matter content from Image 3.
8. The method of any preceding or following embodiment/feature/aspect, further comprising:
   (p) selecting regions of interest of pixels from Image 3 wherein such regions of interest have combinations of properties of interest comprising relatively high porosity and high organic matter,
   (q) imaging physical locations of regions of interest of pixels from Image 3 wherein such regions of interest have combinations of properties of interest comprising relatively high porosity and high organic matter content with a FIB SEM using two or more detectors, (r) creating 3D digital images from the two or more detector images, (s) segmenting the two or more digital detector images to identify voxels as pore, rock or organic matter, and (t) estimating rock properties from the segmented two or more images.

9. The method of any preceding or following embodiment/feature/aspect, wherein Sample 1 comprises a well core, drill cuttings or similar samples of porous media.

10. The method of any preceding or following embodiment/feature/aspect, wherein the dual energy X-ray CT scan of Sample 1 is performed with a nominal resolution from about 0.2 mm to about 0.5 mm.

11. The method of any preceding or following embodiment/feature/aspect, wherein selecting a region of interest of the Slices of Image 1 comprising low values of RhoB and $Z_{eff}$ comprises plotting pairs of values of RhoB and $Z_{eff}$ on Cartesian coordinates, dividing the pairs of values of RhoB and $Z_{eff}$ into four quadrants each quadrant containing approximately equal number of pairs of values of RhoB and $Z_{eff}$ and selecting pairs of values of RhoB and $Z_{eff}$ from the quadrant containing low values of RhoB and low values of $Z_{eff}$ relative to the other quadrants.

12. The method of any preceding or following embodiment/feature/aspect, wherein creating physical sub-samples from selected Slices of Sample 1 comprises extracting plugs or chips from Sample 1.

13. The method of any preceding or following embodiment/feature/aspect, wherein the plugs or chips from Sample 1 are substantially cylindrical in shape.

14. The method of any preceding or following embodiment/feature/aspect, wherein the plugs or chips from Sample 1 have length of 1 cm to 5 cm and a diameter of 2 cm to 4 cm.

15. The method of any preceding or following embodiment/feature/aspect, wherein the scanning Sample 2 with a micro CT X-ray scanner or a dual energy micro CT scanner is performed with a nominal resolution of 10 μM to 100 μM.

16. The method of any preceding or following embodiment/feature/aspect, wherein Sample 3 comprises tiles that are mechanically cut from Sample 1.

17. The method of any preceding or following embodiment/feature/aspect, wherein the size of the tiles are 2 mm×2 mm×400 μM to 6 mm×6 mm×600 μM.

18. The method of any preceding or following embodiment/feature/aspect, wherein Sample 3 comprises 1 to 5 samples or more selected from each plug.

19. The method of any preceding or following embodiment/feature/aspect, wherein preparing Sample 3 for SEM imaging comprises mechanical polishing.

20. The method of any preceding or following embodiment/feature/aspect, wherein preparing Sample 3 for SEM imaging comprises ion beam polishing.

21. The method of any preceding or following embodiment/feature/aspect, wherein creating 2D digital images (Image 3) of Sample 3 using an SEM is performed with nominal resolution of 5 to 30 nanometers and with a field of view of 15,000×15,000 nanometers to 30,000×30,000 nanometers.

22. The method of any preceding or following embodiment/feature/aspect, wherein creating 2D digital images (Image 3) further comprises an EDS spectrum.

23. The method of any preceding or following embodiment/feature/aspect, wherein the EDS comprises estimates of but not limited to, clay, organic matter, calcite, quartz, plagioclase, pyrite, titanium dioxide, or any combinations thereof.

24. The method of any preceding or following embodiment/feature/aspect, wherein imaging physical locations of regions of interest of pixels from Image 3 using SE-2 and ESB detectors is performed with nominal resolution of 5 to 15 nanometers and with a field of view of 5,000×5,000 nanometers to 30,000×30,000 nanometers.

25. The method of any preceding or following embodiment/feature/aspect, wherein creating 3D digital images from the SE-2 and ESB detector images comprises multiple 2D images.

26. The method of any preceding or following embodiment/feature/aspect, wherein the multiple 2D images comprises removing a layer of Sample 3 as with milling by a focused ion beam, scanning the exposed surface, and storing a digital image of the scan.

27. The method of any preceding or following embodiment/feature/aspect, wherein the layer milled by a focused ion beam is 5 to 15 nanometers thick.

28. The method of any preceding or following embodiment/feature/aspect, wherein the 3D digital image comprises 500 to 800 2D images.

29. The method of any preceding or following embodiment/feature/aspect, wherein 500 to 800 2D images are aligned to produce a 3D image.

30. The method of any preceding or following embodiment/feature/aspect, wherein the rock properties comprises connected porosity, organic matter content, absolute permeability in multiple axes, relative permeability, two-phase relative permeability, capillary pressure, grain size distribution, electrical properties, or elastic properties, or any combinations thereof.

31. The method of any preceding or following embodiment/feature/aspect, wherein porosity comprises connected porosity, isolated porosity, or total porosity, or any combinations thereof.

32. The method of any preceding or following embodiment/feature/aspect, wherein two phase permeability comprises water-oil permeability, gas-oil permeability, or water-gas displacement, or any combinations thereof.

33. The method of any preceding or following embodiment/feature/aspect, wherein electrical properties comprise formation factor, resistivity index, Archie's constant a, Archie's constant m, or Archie's constant n, or any combinations thereof.

34. The method of any preceding or following embodiment/feature/aspect, wherein elastic properties comprise Poisson's ratio, elastic modulus, hydraulic conductivity, or specific gravity, or any combinations thereof.

35. The method of any preceding or following embodiment/feature/aspect, wherein capillary pressure comprises capillary pressure values at each saturation for primary drainage, capillary pressure values at each saturation for imbibitions, and capillary pressure values at each saturation for secondary drainage cycles.

36. The method of any preceding or following embodiment/feature/aspect, wherein elastic properties comprises compressional velocity, shear velocity, Lamé's parameters, Young's modulus, bulk modulus, Poisson's ratio, or any combinations thereof.

37. The method of any preceding or following embodiment/feature/aspect, further comprising upscaling the rock properties.

38. The method of any preceding or following embodiment/feature/aspect, wherein the upscaling comprises sub-dividing the segmented 3D images into sub-images, estimating rock properties for each of the sub-images, establishing a best fit correlation between pairs of selected rock properties, and using the best fit correlation between pairs of selected rock properties to characterize the rock properties of the facies or formation from which Sample 1 was taken.

39. The method of any preceding or following embodiment/feature/aspect, wherein the upscaling comprises correlating selected pairs of estimated rock properties with physical locations on Sample 1, Sample 2 and/or Sample 3; assigning the remaining estimates of rock properties to corresponding sections of Sample 1, Sample 2 and/or Sample 3; and using the assigned estimates of rock properties in a well simulation or reservoir simulation model.

40. The method of any preceding or following embodiment/feature/aspect, wherein the upscaling comprises estimating rock properties of drill cuttings and correlating the drill cuttings with the physical well location from which the drill cuttings were retrieved.

41. A system for estimating selected physical properties of a rock sample, comprising:
    (a) a sample of a porous medium such as rock,
    (b) a dual energy X-ray CT scanner,
    (c) a micro X-ray CT scanner or a second dual energy micro X-ray CT scanner,
    (d) cutting, milling or shaping devices to extract samples of porous media,
    (e) grinders, millers, polishers or similar devices to prepare the surface of the porous media,
    (f) an ion beam polisher,
    (g) a scanning electron microscope, and
    (h) one or more computer systems.

42. The system of any preceding or following embodiment/feature/aspect, wherein the SEM further comprises an energy dispersive x-ray scanner.

43. The system of any preceding or following embodiment/feature/aspect, wherein the SEM further comprises more than one detector including an SE-2 detector or an ESB detector or both.

44. The system of any preceding or following embodiment/feature/aspect, wherein the SEM further comprises a focused ion beam capable of milling the surface of a sample.

45. The system of any preceding or following embodiment/feature/aspect, wherein the one or more computer systems comprises software to capture images, process images, segment images, estimate rock properties, or any combinations thereof.

46. A method for qualitative facies analysis and selecting a subsample for estimating selected physical properties of a rock sample, comprising:
    a) estimating values of the bulk density, RhoB, and effective atomic number, $Z_{\textit{eff}}$, for layers of voxels (Slices) in 3D digital tomographic images (Image 1) of a physical sample (Sample 1),
    b) plotting pairs of the values of RhoB and $Z_{\textit{eff}}$ on a cross plot,
    c) dividing the crossplot into a plurality of quadrants, and
    d) selecting pairs of values of RhoB and $Z_{\textit{eff}}$ from one of the plurality of quadrants which correspond to a selected region of interest of the Slices of Image 1.

47. The method of any preceding or following embodiment/feature/aspect, wherein the plurality of quadrants comprises four quadrants I, II, III and IV.

48. The method of any preceding or following embodiment/feature/aspect, wherein the quadrant I comprises data pairs having i) similar values of RhoB and lower values of $Z_{\textit{eff}}$ than the quadrant II, ii) lower values of RhoB and lower values of $Z_{\textit{eff}}$ than the quadrant III, and iii) lower values of RhoB and similar values of $Z_{\textit{eff}}$ than quadrant IV.

49. The method of any preceding or following embodiment/feature/aspect, wherein the data pairs within quadrant I correspond to slices having at least one of higher porosity and higher organic content than the data pairs within any of quadrants II, III, and IV.

50. The method of any preceding or following embodiment/feature/aspect, wherein each quadrant contains at least one pair of values of RhoB and $Z_{\textit{eff}}$.

51. The method of any preceding or following embodiment/feature/aspect, wherein the dividing of the pairs of values of RhoB and $Z_{\textit{eff}}$ into the plurality of quadrants provides a total number of pairs of values of RhoB and $Z_{\textit{eff}}$ in each of the quadrants that is within ±10% of a total number of pairs of values of RhoB and $Z_{\textit{eff}}$ in any other of the quadrants.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It will be apparent to those skilled in the art that various modifications and variations can be made to the embodiments of the present invention without departing from the spirit or scope of the present invention. Thus, it is intended that the present invention covers other modifications and variations of this invention provided they come within the scope of the appended claims and their equivalents.

What is claimed is:

1. A method for estimating selected physical properties of a rock sample, comprising:
    (a) preparing a rock sample,
    (b) creating a digital image of the rock sample by scanning the rock sample,
    (c) estimating selected physical properties of the rock sample from the digital image of the rock sample,
    (d) determining if the digital image provides sufficient detail for estimation of final rock properties, wherein step (e) directly follows step (d) if sufficient detail is not determined to be provided and step (j) directly follows if sufficient detail is determined to be provided, wherein steps (e) through (i) are used at least once,
    (e) identifying one or more regions within the rock sample that contain high porosity and/or organic matter content,
    (f) selecting subsamples of the rock sample that contain high porosity and/or organic content,
    (g) preparing rock subsamples from the selected subsamples,
    (h) increasing the resolution of the scanning of the rock sample, (i) repeating steps (b) through (d) until a desired resolution is achieved, and
(j) estimating final rock properties.

2. The method of claim 1, wherein the rock sample comprises organic mud rock, shale, carbonate, sandstone, limestone, dolostone, or any combinations thereof.

3. The method of claim 1, wherein preparing the rock subsamples comprises cutting, abrading, shaping milling, focused ion beam polishing, or any combinations thereof.

4. The method of claim 1, wherein the digital image comprises a two-dimensional (2D) image or a three-dimensional (3D) image.

5. The method of claim 1, wherein creating a digital image of the rock sample by scanning the rock sample at a selected resolution comprises X-ray computed tomography, dual energy X-ray computed tomography, X-ray projection, scanning electron microscopy (SEM), focused ion beam scanning electron microscopy (FIB-SEM), or any combinations thereof.

6. The method of claim 1, wherein physical properties of the rock sample comprise porosity, organic matter content, absolute permeability in at least one axis, relative permeability, two-phase relative permeability, capillary pressure, grain size distribution, electrical properties, elastic properties, or any combinations thereof.

7. A method for estimating selected physical properties of a rock sample, comprising:
(a) acquiring a physical sample of a porous medium (Sample 1),
(b) performing a dual energy X-ray CT scan of Sample 1,
(c) creating 3D digital images (Image 1) of Sample 1 from the dual energy X-ray CT scan,
(d) calculating the bulk density, RhoB, and effective atomic number, $Z_{eff}$, for each layer of voxels (Slices) in Image 1,
(e) selecting a region of interest of the Slices of Image 1 comprising selected values of RhoB and $Z_{eff}$,
(f) creating physical sub-samples (Sample 2) from selected Slices of Sample 1 wherein the Slices comprise selected values of RhoB and $Z_{eff}$,
(g) scanning Sample 2 with a micro CT X-ray scanner or imaging Sample 2 using a micro X-ray projection,
(h) creating 2D or 3D digital images (Image 2) of Sample 2,
(i) calculating porosity or RhoB and $Z_{eff}$ of Image 2,
(j) selecting regions of interest of pixels or voxels from Image 2 wherein such regions of interest have relatively high porosity or selected values of RhoB and $Z_{eff}$ (Image 2),
(k) creating sub-samples (Sample 3) from the physical locations corresponding to Image 2,
(l) preparing Sample 3 for SEM imaging,
(m) creating 2D digital images (Image 3) of Sample 3 using an SEM or SEM with EDS capability,
(n) estimating porosity of Image 3, and
(o) estimating organic matter content from Image 3.

8. The method of claim 7, further comprising:
(p) selecting regions of interest of pixels from Image 3 wherein such regions of interest have combinations of properties of interest comprising relatively high porosity and high organic matter,
(q) imaging physical locations of regions of interest of pixels from Image 3 wherein such regions of interest have combinations of properties of interest comprising relatively high porosity and high organic matter content with a FIB SEM using two or more detectors,
(r) creating 3D digital images from the two or more detector images,
(s) segmenting the two or more digital detector images to identify voxels as pore, rock or organic matter, and
(t) estimating rock properties from the segmented two or more detector images.

9. The method of claim 8, wherein imaging physical locations of regions of interest of pixels from Image 3 using detectors is performed with nominal resolution of 5 to 15 nanometers and with a field of view of 5,000×5,000 nanometers to 30,000×30,000 nanometers.

10. The method of claim 8, wherein creating 3D digital images from the detector images comprises multiple 2D images.

11. The method of claim 10, wherein the multiple 2D images comprises removing a layer of Sample 3 as with milling by a focused ion beam, scanning the exposed surface, and storing a digital image of the scan.

12. The method of claim 11, wherein the layer milled by a focused ion beam is 5 to 15 nanometers thick.

13. The method of claim 8, wherein the 3D digital image comprises 500 to 800 2D images.

14. The method of claim 13, wherein 500 to 800 2D images are aligned to produce a 3D image.

15. The method of claim 8, wherein the rock properties comprises connected porosity, organic matter content, absolute permeability in multiple axes, relative permeability, two-phase relative permeability, capillary pressure, grain size distribution, or electrical properties, elastic properties, or any combinations thereof.

16. The method of claim 15, wherein porosity comprises connected porosity, isolated porosity, or total porosity, or any combinations thereof.

17. The method of claim 15, wherein two phase permeability comprises water-oil permeability, gas-oil permeability, or water-gas displacement, or any combinations thereof.

18. The method of claim 15, wherein electrical properties comprise formation factor, resistivity index, Archie's constant a, Archie's constant m, or Archie's constant n, or any combinations thereof.

19. The method of claim 15, wherein elastic properties comprise Poisson's ratio, elastic modulus, hydraulic conductivity, or specific gravity, or any combinations thereof.

20. The method of claim 15, wherein capillary pressure comprises capillary pressure values at each saturation for primary drainage, capillary pressure values at each saturation for imbibitions, and capillary pressure values at each saturation for secondary drainage cycles.

21. The method of claim 15, wherein elastic properties comprises compressional velocity, shear velocity, Lame's parameters, Young's modulus, bulk modulus, Poisson's ratio, or any combinations thereof.

22. The method of claim 8, further comprising upscaling the rock properties.

23. The method of claim 22, wherein the upscaling comprises sub-dividing the segmented 3D images into sub-images, estimating rock properties for each of the sub-images, establishing a best fit correlation between pairs of selected rock properties, and using the best fit correlation between pairs of selected rock properties to characterize the rock properties of the facies or formation from which Sample 1 was taken.

24. The method of claim 22, wherein the upscaling comprises correlating selected pairs of estimated rock properties with physical locations on Sample 1, Sample 2 and/or Sample 3; assigning the remaining estimates of rock properties to corresponding sections of Sample 1, Sample 2 and/or Sample 3; and using the assigned estimates of rock properties in a well simulation or reservoir simulation model.

25. The method of claim 22, wherein the upscaling comprises estimating rock properties of drill cuttings and correlating the drill cuttings with the physical well location from which the drill cuttings were retrieved.

26. The method of claim 7, wherein Sample 1 comprises a well core, drill cuttings or similar samples of porous media.

27. The method of claim 7, wherein the dual energy X-ray CT scan of Sample 1 is performed with a nominal resolution from about 0.2 mm to about 0.5 mm.

28. The method of claim 7, wherein selecting a region of interest of the Slices of Image 1 comprising low values of RhoB and $Z_{eff}$ comprises plotting pairs of values of RhoB and $Z_{eff}$ on Cartesian coordinates, dividing the pairs of values of RhoB and $Z_{eff}$ into four quadrants each quadrant containing approximately equal number of pairs of values of RhoB and $Z_{eff}$ and selecting pairs of values of RhoB and $Z_{eff}$ from the quadrant containing low values of RhoB and low values of $Z_{eff}$ relative to the other quadrants.

29. The method of claim 7, wherein creating physical subsamples from selected Slices of Sample 1 comprises extracting plugs or chips from Sample 1.

30. The method of claim 29, wherein the plugs or chips from Sample 1 have length from about 1 cm to about 5 cm and a diameter from about 2 cm to about 4 cm.

31. The method of claim 29, wherein the plugs or chips from Sample 1 are substantially cylindrical in shape.

32. The method of claim 7, wherein the scanning Sample 2 with a micro CT X-ray scanner or a dual energy micro CT scanner is performed with a nominal resolution of 10 μm to 100 μm.

33. The method of claim 7, wherein Sample 3 comprises tiles that are mechanically cut from Sample 1.

34. The method of claim 33, wherein the size of the tiles are 2 mm×2 mm×400 μm to 6 mm×6 mm×600 μm.

35. The method of claim 7, wherein Sample 3 comprises 1 to 5 samples or more selected from each plug.

36. The method of claim 7, wherein preparing Sample 3 for SEM imaging comprises mechanical polishing.

37. The method of claim 7, wherein preparing Sample 3 for SEM imaging comprises ion beam polishing.

38. The method of claim 7, wherein creating 2D digital images (Image 3) of Sample 3 using an SEM is performed with nominal resolution of 5 to 30 nanometers and with a field of view of 15,000×15,000 nanometers to 30,000×30,000 nanometers.

39. The method of claim 7, wherein creating 2D digital images (Image 3) further comprises an EDS spectrum.

40. The method of claim 39, wherein the EDS comprises estimates of clay, organic matter, calcite, quartz, plagioclase, pyrite, titanium dioxide, or any combinations thereof.

41. A system for estimating selected physical properties of a rock sample, comprising:
(a) a sample of a porous medium such as rock,
(b) a dual energy X-ray CT scanner,
(c) a micro X-ray CT scanner or a second dual energy micro X-ray CT scanner,
(d) cutting, milling or shaping devices to extract samples of porous media,
(e) grinders, millers, polishers or similar devices to prepare the surface of the porous media,
(f) an ion beam polisher,
(g) a scanning electron microscope, and
(h) one or more computer systems, wherein the one or more computer systems comprises a non-transitory computer-readable medium encoded with a computer program to capture images, process images, segment images, estimate rock properties, and perform computations of steps of i) creating a digital image of the rock sample by scanning the rock sample, ii) estimating selected physical properties of the rock sample from the digital image of the rock sample, iii) determining if the digital image provides sufficient detail for estimation of final rock properties, iv) identifying one or more regions within the rock sample that contain high porosity and/or organic matter content, or v) selecting subsamples of the rock sample that contain high porosity and/or organic content.

42. The system of claim 41, wherein the SEM further comprises an energy dispersive x-ray scanner.

43. The system of claim 41, wherein the SEM further comprises more than one detector including an SE-2 detector or an ESB detector or both.

44. The system of claim 41, wherein the SEM further comprises a focused ion beam capable of milling the surface of a sample.

45. A method for qualitative facies analysis and selecting a subsample for estimating selected physical properties of a rock sample, comprising:
a) estimating values of the bulk density, RhoB, and effective atomic number, $Z_{eff}$, for layers of voxels (Slices) in 3D digital tomographic images (Image 1) of a physical sample (Sample 1),
b) plotting pairs of the values of RhoB and $Z_{eff}$ on a cross plot,
c) dividing the crossplot into a plurality of quadrants,
d) selecting pairs of values of RhoB and $Z_{eff}$ from one of the plurality of quadrants which correspond to a selected region of interest of the Slices of Image 1.

46. The method of claim 45, wherein the plurality of quadrants comprises four quadrants I, II, III and IV.

47. The method of claim 46, wherein the quadrant I comprises data pairs having i) similar values of RhoB and lower values of $Z_{eff}$ than the quadrant II, ii) lower values of RhoB and lower values of $Z_{eff}$ than the quadrant III, and iii) lower values of RhoB and similar values of $Z_{eff}$ than quadrant IV.

48. The method of claim 47, wherein the data pairs within quadrant I correspond to slices having at least one of higher porosity and higher organic content than the data pairs within any of quadrants II, III, and IV.

49. The method of claim 45, wherein each quadrant contains at least one pair of values of RhoB and $Z_{eff}$.

50. The method of claim 49, wherein the dividing of the pairs of values of RhoB and $Z_{eff}$ into the plurality of quadrants provides a total number of pairs of values of RhoB and $Z_{eff}$ in each of the quadrants that is within ±10% of a total number of pairs of values of RhoB and $Z_{eff}$ in any other of the quadrants.

* * * * *